(12) United States Patent
Haick et al.

(10) Patent No.: US 9,625,341 B2
(45) Date of Patent: Apr. 18, 2017

(54) PLATFORM UNIT FOR COMBINED SENSING OF PRESSURE, TEMPERATURE AND HUMIDITY

(71) Applicant: Technion Research & Development Foundation Limited, Haifa (IL)

(72) Inventors: Hossam Haick, Haifa (IL); Gregory Shuster, Ramat Ishay (IL); Meital Segev-Bar, Haifa (IL); Victoria Kloper, Haifa (IL); Sagi Gliksman, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 198 days.

(21) Appl. No.: 14/387,838

(22) PCT Filed: Mar. 21, 2013

(86) PCT No.: PCT/IB2013/052235
§ 371 (c)(1),
(2) Date: Sep. 24, 2014

(87) PCT Pub. No.: WO2013/144788
PCT Pub. Date: Oct. 3, 2013

(65) Prior Publication Data
US 2015/0082920 A1 Mar. 26, 2015

Related U.S. Application Data

(60) Provisional application No. 61/615,475, filed on Mar. 26, 2012, provisional application No. 61/783,614, filed on Mar. 14, 2013.

(51) Int. Cl.
*B82Y 15/00* (2011.01)
*G01L 19/00* (2006.01)
(Continued)

(52) U.S. Cl.
CPC .......... *G01L 19/0092* (2013.01); *B82Y 15/00* (2013.01); *G01K 7/186* (2013.01);
(Continued)

(58) Field of Classification Search
CPC ....... G01L 9/0058; G01L 9/025; G01L 9/046; G01L 9/065; G01L 1/2281; G01L 19/0092; G01K 2211/00; B82Y 15/00
(Continued)

(56) References Cited

U.S. PATENT DOCUMENTS 6,773,926 B1   8/2004 Freund
7,357,035 B2 *  4/2008 Liu ........................... G01F 1/28
                                                 374/E7.023

(Continued)

FOREIGN PATENT DOCUMENTS

CN    1184530    6/1998
CN    2570782    9/2003

(Continued)

OTHER PUBLICATIONS

Zilberman et al., (2010) Carbon nanotube/hexa-peri-hexabenzocoronene bilayers for discrimination between nonpolar volatile organic compounds of cancer and humid atmospheres. Adv Mater 22(38): 4317-4320.

(Continued)

*Primary Examiner* — Justin Olamit
(74) *Attorney, Agent, or Firm* — Roach Brown McCarthy & Gruber, P.C.; Kevin D. McCarthy

(57) ABSTRACT

The present invention provides a modular platform unit comprising a plurality of sensors for the combined sensing of pressure, temperature and humidity. In particular, the sensors are composed of a layer of metallic-capped nanoparticles (MCNP) casted on a flexible substrate or a rigid
(Continued)

substrate. Integration of the platform unit for artificial or electronic skin applications is disclosed.

19 Claims, 22 Drawing Sheets

(51) Int. Cl.
　　　G01N 27/12　　　(2006.01)
　　　G01K 7/18　　　(2006.01)
　　　G01L 1/22　　　(2006.01)
(52) U.S. Cl.
　　　CPC ....... *G01N 27/121* (2013.01); *G01K 2211/00* (2013.01); *G01L 1/2281* (2013.01)
(58) Field of Classification Search
　　　USPC .......................................................... 73/708
　　　See application file for complete search history.

(56) References Cited

U.S. PATENT DOCUMENTS

| | | | | |
|---|---|---|---|---|
| 9,080,942 | B2* | 7/2015 | Zhong | B82Y 15/00 |
| 2005/0241935 | A1 | 11/2005 | Lewis | |
| 2009/0148690 | A1 | 6/2009 | Krasteva | |
| 2010/0191474 | A1 | 7/2010 | Haick | |
| 2011/0019373 | A1 | 1/2011 | Ryhanen et al. | |
| 2012/0062245 | A1 | 3/2012 | Bao et al. | |
| 2012/0245434 | A1 | 9/2012 | Haick et al. | |
| 2012/0245854 | A1 | 9/2012 | Haick et al. | |
| 2013/0034910 | A1 | 2/2013 | Haick et al. | |
| 2013/0171733 | A1* | 7/2013 | Haick | G01N 30/00 436/39 |
| 2015/0268692 | A1 | 9/2015 | Viallet | |

FOREIGN PATENT DOCUMENTS

| | | | |
|---|---|---|---|
| CN | 1498345 | | 5/2004 |
| TW | 2005-31124 A | * | 9/2005 |
| WO | WO0000808 | | 1/2000 |
| WO | 2007057905 | | 5/2007 |
| WO | 2009066293 A1 | | 5/2009 |
| WO | WO2009118739 A1 | | 10/2009 |
| WO | WO2010079490 A1 | | 7/2010 |
| WO | WO2011148371 A1 | | 12/2011 |
| WO | WO2012023138 A2 | | 2/2012 |
| WO | WO2012169655 A1 | | 12/2012 |

OTHER PUBLICATIONS

Zilberman et al., (2011) Nanoarray of Polycyclic Aromatic Hydrocarbons and Carbon Nanotubes for Accurate and Predictive Detection in Real-World Environmental Humidity. ACS Nano 5(8): 6743-6753.
Konvalina et al., (2012) Effect of Humidity on Nanoparticle-Based Chemiresistors: A Comparison between Synthetic and Real-World Samples. ACS Appl Mater Interlaces 4(1): 317-325.
Lacour et al., (2011) Elastic components for prosthetic skin. Conf Proc IEEE Eng Med Biol Soc 2011: 8373-6.
Lee and Nicholls (1999) Review Article Tactile sensing for mechatronics—a state of the art survey. Mechatronics 9(1): 1-31.
Lee et al., (2007) Uniformly dispersed deposition of colloidal nanoparticles and nanowires by boiling. Appl Phys Lett 91: 173112.
Linko et al., (2011) Defined-size DNA triple crossover construct for molecular electronics: modification, positioning and conductance properties. Nanotechnology 22(27): 275610 (7 pages).
Lopez-Higuera et al., (2011) Fiber Optic Sensors in Structural Health Monitoring. Journal of Lightwave Technology 29 (4): 587-608.
Maenosono et al., (2003) Overview of Nanoparticle Array Formation by Wet Coating. Journal of Nanoparticle Research 5(1): 5-15.
Maheshwari et al., (2006) High-Resolution Thin-Film Device to Sense Texture by Touch. Science 312(5779): 1501-1504.
Makishima and Mackenzie (1973) Direct calculation of Young's moidulus of glass. Journal of Non-Crystalline Solids 12 (1): 35-45.
Mannsfeld et al., (2010) Highly sensitive flexible pressure sensors with microstructured rubber dielectric layers. Nature Mater 9: 859-864.
Marom et al., (2012) Gold Nanoparticle Sensors for Detecting Chronic Kidney Disease and Disease Progression. Nanomedicine (Lond) 7(5): 639-650.
Matsuzaki et al., (2008) Rubber-based strain sensor fabricated using photolithography for intelligent tires. Sensors and Actuators A: Physical 148(1): 1-9.
Mokari (2011) Synthesis and characterization of hybrid nanostructures Nano Rev 2: 5983 (9 pages).
Murphy et al., (2005) Anisotropic Metal Nanoparticles: Synthesis, Assembly, and Optical Applications. J Phys Chem B 109(29): 13857-13870.
Nath and Chilkoti (2002) A colorimetric gold nanoparticle biosensor: effect of particle size on sensitivity. In: Engineering in Medicine and Biology, 2002. 24th Annual Conference and the Annual Fall Meeting of the Biomedical Engineering Society EMBS/BMES Conference, 2002. Proceedings of the Second Joint. vol. 1 pp. 574-575.
Olichwer et al., (2012) Cross-Linked Gold Nanoparticles on Polyethylene: Resistive Responses to Tensile Strain and Vapors. ACS Appl Mater Interlaces 4(11): 6151-6161.
Pang et al., (2012) A flexible and highly sensitive strain-gauge sensor using reversible interlocking of nanofibers. Nature Mater 11: 795-801.
Paska et al., (2011) Enhanced Sensing of Nonpolar VolatileOrganic Compounds by SiliconNanowire Field Effect Transistors. ACS Nano 5(7): 5620-5626.
Paska et al., (2012) Molecular Gating of Silicon Nanowire Field-Effect Transistors with Nonpolar Analytes. ACS Nano 6 (1): 335-345.
Pavanello et al., (2010) Modeling Hole Transport in Wet and Dry DNA. J Phys Chem B 114(13): 4416-4423.
Peng et al., (2009) Diagnosing lung cancer in exhaled breath using gold nanoparticles. Nature Nanotech 4: 669-673.
Peng et al., (2010) Detection of lung, breast, colorectal, and prostate cancers from exhaled breath using a single array of nanosensors. Br J Cancer 103(4): 542-551.
Power et al., (2010) Silver nanoparticle polymer composite based humidity sensor. Analyst 135: 1645-1652.
Raguse et al., (2009) Gold Nanoparticle Chemiresistor Sensors in Aqueous Solution: Comparison of Hydrophobic and Hydrophilic Nanoparticle Films. J Phys Chem C 113(34): 15390-15397.
Rogers et al., (2009) A curvy, stretchy future for electronics. Proc Natl Acad Sci U S A 106(27): 10875-6.
Rowe et al., (2004) Single-Phase Synthesis of Functionalized Gold Nanoparticles. Chem Mater 16(18): 3513-3517.
Ryan et al., (2011) On the "U-shaped" continuum of band edge states at the Si/SiO2 interface. Applied Physical Letters 99: 223518 (3 pages).
Segev-Bar et al., (2012) Effect of Perforation on the Sensing Properties of Monolayer-Capped Metallic Nanoparticle Films. J Phys Chem C 116(29): 15361-15368.
Sekitani et al., (2008) A Rubberlike Stretchable Active Matrix Using Elastic Conductors. Science 321(5895): 1468-1472.
Shamanna et al., (2006) Micromachined integrated pressure—thermal sensors on flexible substrates. Journal of Micromechanics and Microengineering 16: 1984-1992.
Shuster et al., (2011) Classification of Breast Cancer Precursors through Exhaled Breath, Breast Cancer Research and Treatment. Breast Cancer Res Treat 126(3): 791-796.
Siffalovic et al., (2010) Towards strain gauges based on a self-assembled nanoparticle monolayer—SAXS study. Nanotechnology 21(38): 385702 (5 pages).
Someya et al., (2004) A large-area, flexible pressure sensor matrix with organic field-effect transistors for artificial skin applications. Proc Nati Acad Sci U S A 101(27): 9966-70.

(56) References Cited

OTHER PUBLICATIONS

Steinecker et al., (2007) Model of Vapor-Induced Resistivity Changes in Gold—Thiolate Monolayer-Protected Nanoparticle Sensor Films. Anal Chem 79(13): 4977-4986.
Takei et al., (2010) Nanowire active-matrix circuitry for low-voltage macroscale artificial skin. Nature Mater 9: 821-826.
Tisch and Haick (2010) Nanomaterials for cross-reactive sensor arrays. MRS Bull 35(10): 797-803.
Tiwana et al., (2012) A review of tactile sensing technologies with applications in biomedical engineering. Sensors and Actuators A: Physical 179: 17-31.
Vossmeyer et al., (2008) Networked Gold-Nanoparticle Coatings on Polyethylene: Charge Transport and Strain Sensitivity. Advanced Functional Materials 18(11): 1611-1616.
Walker (2012) A review of technologies for sensing contact location on the surface of a display. Journal of the Society for Information Display 20(8): 413-440.
Wang et al., (2007) Correlation between nanostructural parameters and conductivity properties for molecularly-mediated thin film assemblies of gold nanoparticle. J Mater Chem 17(5): 457-462.
Wang et al., (2010) Thin Film Assemblies of Molecularly-Linked Metal Nanoparticles and Multifunctional Properties. Langmuir 26(2): 618-632.
Wuelfing and Murray (2002) Electron Hopping through Films of Arenethiolate Monolayer-Protected Gold Clusters. J Phys Chem B 106(12): 3139-3145.
Wuelfing et al., (2000) Electronic Conductivity of Solid-State, Mixed-Valent, Monolayer-Protected Au Clusters. J Am Chem Soc 122(46): 11465-11472.
Yao et al., (2010) A capacitive humidity sensor based on gold—PVA core-shell nanocomposites. Sensors and Actuators B: Chemical 145(1): 327-333.
Yeh and Tseng (1989) Analysis of the d.c. and a.c. properties of K2O-doped porous Ba0.5Sr0.5TiO3 ceramic humidity sensor. J Mater Sci 24(8): 2739-2745.
Zabet-Khosousi and Dhirani (2008) Charge Transport in Nanoparticle Assemblies. Chem Rev 108(10): 4072-4142.
Zhang and Srinivasan (2008) Layer-by-layer assembled gold nanoparticle films on amine-terminated substrates. J Coll Interf Sci 319(2): 450-456.
Alvares et al., (2011) Nanoparticle films as biomimetic tactile sensors. Procedia Engineering 25: 1349-1352.
American Thoracic Society (ATS) and the European Respiratory Society (ERS). ATS/ERS recommendations for standardized procedures for the online and offline measurement of exhaled lower respiratory nitric oxide and nasal nitric oxide, 2005. Am J Respir Crit Care Med 171(8): 912-930.
Anderson and Parks (1968) Electrical conductivity of silica gel in the presence of adsorbed water. J Phys Chem 72 (10): 3662-3668.
Arregui et al., (2002) Simultaneous measurement of humidity and temperature by combining a reflective intensity-based optical fiber sensor and a fiber Bragg grating. IEEE Sensors J 2(5): 482-487.
Barash et al., (2009) Sniffing the Unique "Odor Print" of Non-Small-Cell Lung Cancer with Gold Nanoparticles. Small 5 (22): 2618-2624.
Barash et al., (2012) Classification of lung cancer histology by gold nanoparticle sensors. Nanomedicine 8(5): 580-589.
Bay et al., (1995) Design of the "army-ant" cooperative lifting robot. IEEE Robotics & Automation Magazine 2(1): 36-43.
Boland (2010) Flexible electronics: Within touch of artificial skin. Nat Mater 9(10): 790-2.
Brown et al., (2005) Evaluation of polydimethylsiloxane scaffolds with physiologically-relevant elastic moduli: interplay of substrate mechanics and surface chemistry effects on vascular smooth muscle cell response. Biomaterials 26(16): 3123-3129.
Brust and Kiely (2002) Some recent advances in nanostructure preparation from gold and silver particles: a short topical review. Colloids and Surfaces A: Physicochemical and Engineering Aspects 202(2-3): 175-186.
Brust et al., (1994) Synthesis of thiol-derivatised gold nanoparticles in a two-phase Liquid—Liquid system. J Chem Soc Chem Commun 1994: 801-802.
Cheng et al., (2009) A flexible capacitive tactile sensing array with floating electrodes. Journal of Micromechanics and Microengineering 19: 115001 (10 pages).
Cheng et al., (2012) A Wireless Sensor System for Prognostics and Health Management. IEEE Sensors Journal 10(4): 856-862.
Chow et al., (2009) Detection of organics in aqueous solution using gold nanoparticles modified with mixed monolayers of 1-hexanethiol and 4 mercaptophenol. Sens Actuat B 143(2): 704-711.
Cook et al., (2009) Ambient intelligence: Technologies, applications, and opportunities. Pervasive and Mobile computing 5: 277-298.
Cooper et al., (2010) Gold nanoparticle chemiresistor sensor array that differentiates between hydrocarbon fuels dissolved in artificial seawater. Anal Chem 82(9): 3788-3795.
Cosseddu et al., (2012) Strain Sensitivity and Transport Properties in Organic Field-Effect Transistors. IEEE Elec Dev Lett 33(1): 113-115.
Daniel and Astruc (2004) Gold nanoparticles: assembly, supramolecular chemistry, quantum-size-related properties, and applications toward biology, catalysis, and nanotechnology. Chem Rev 104(1): 293-346.
Dargahi and Najarian (2004) Human tactile perception as a standard for artificial tactile sensing—a review. Int J Med Robot 1(1): 23-35.
Dasog and Scott (2007) Understanding the oxidative stability of gold monolayer-protected clusters in the presence of halide ions under ambient conditions. Langmuir 23(6): 3381-3387.
Deegan (2000) Pattern formation in drying drops. Phys Rev E Stat Phys Plasmas Fluids Relat Interdiscip Topics 61(1): 475-85.
Deegan et al., (1997) Capillary flow as the cause of ring stains from dried liquid drops. Nature 389: 827-828.
Deegan et al., (2000) Contact line deposits in an evaporating drop. Phys Rev E Stat Phys Plasmas Fluids Relat Interdiscip Topics 62(1 Pt B): 756-65.
Dovgolevsky et al., (2009) Chemically Sensitive Resistors Based on Monolayer-Capped Cubic Nanoparticles: Towards Configurable Nanoporous Sensors. Small 5(10): 1158-1161.
Dovgolevsky et al., (2010) Monolayer-Capped Cubic Platinum Nanoparticles for Sensing Nonpolar Analytes in Highly Humid Atmospheres. J Phys Chem C114(33): 14042-14049.
Eltaib and Hewit (2003) Tactile sensing technology for minimal access surgery—a review. Mechatronics 13: 1163-1177.
Engel et al., (2003) Development of polyimide flexible tactile sensor skin. Journal of Micromechanics and Microengineering 13: 359-366.
Farcau et al., (2011) High-sensitivity strain gauge based on a single wire of gold nanoparticles fabricated by stop-and-go convective self-assembly. ACS Nano 5(9): 7137-43.
Farcau et al., (2011) Monolayered Wires of Gold Colloidal Nanoparticles for High-Sensitivity Strain Sensing. J Phys Chem C 115(30): 14494-14499.
Farserotu et al., (2012) Smart skin for tactile prosthetics. 6th International Symposium on Medical Information and Communication Technology (ISMICT), IEEE, Mar. 25, 2012 (Mar. 25, 2012), pp. 1-8; XP032183647.
Fischetti (1984) The importance of the anode field in controlling the generation rate of the donor states at the Si—SiO2 Interface. J Appl Phys 56(2): 575-577.
Garg et al., (2010) Robust gold nanoparticles stabilized by trithiol for application in chemiresistive sensors. Nanotechnology 21(40): 405501 (6 pages).
Gorgutsa et al., (2012) A woven 2D touchpad sensor and a 1D slide sensor using soft capacitor fibers. Smart Materials and Structures 21(1): 015010 (10 pages).
Guo et al., (2007) Effect of trace residual ionic impurities on the response of chemiresistor sensors with dithiol-linked monolayer-protected gold (nano)clusters as sensing interfaces. Sens Actuat B 120(2):521-528.

(56) References Cited

OTHER PUBLICATIONS

Ha Dong Han et al., (2002) Humidity effects on the conductance of the assembly of DNA molecules. Chem Phys Lett 355(5-6): 405-409.

Haick (2007) Chemical sensors based on molecularly modified metallic nanoparticles. Journal of Physics D: Applied Physics 40: 7173-7186.

Hakim et al., (2011) Diagnosis of head-and-neck cancer from exhaled breath. Br J Cancer 104(10): 1649-1655.

Han et al., (2001) Core-shell nanostructured nanoparticle films as chemically sensitive interfaces. Anal Chem 73(18): 4441-4449.

Herrmann et al., (2007) Nanoparticle films as sensitive strain gauges. Appl Phys Lett 91: 183105.

Herrmann et al., (2007) Tuning the Coulomb charging energy in cross-linked nanoparticle films. Phys Rev B 76: 212201 (4 pages).

Hostetler et al., (1998) Alkanethiolate Gold Cluster Molecules with Core Diameters from 1.5 to 5.2 nm: Core and Monolayer Properties as a Function of Core Size. Langmuir 14(1): 17-30.

Hsu et al., (2011) A Locally Amplified Strain Sensor Based on a Piezoelectric Polymer and Organic Field-Effect Transistors. IEEE Transactions on Electron Devices 58(3): 910-917.

Huang and Cheng (2009) Design for Low Power and Reliable Flexible Electronics: Self-Tunable Cell-Library Design. Journal of Display Technology 5(6): 206-215.

Joseph et al., (2003) Self-Assembled Gold Nanoparticle/Alkanedithiol Films: Preparation, Electron Microscopy, XPS-Analysis, Charge Transport, and Vapor-Sensing Properties. J Phys Chem B 107(30): 7406-7413.

Joseph et al., (2004) Chemiresistor coatings from Pt- and Au-nanoparticle/nonanedithiol films: sensitivity to gases and solvent vapors. Sens Actuat B 98(2-3): 188-195.

Joseph et al., (2007) Vapor Sensitivity of Networked Gold Nanoparticle Chemiresistors: Importance of Flexibility and Resistivity of the Interlinkage. J Phys Chem C 111(34): 12855-12859.

Joseph et al., (2008) Gold Nanoparticle/Organic Networks as Chemiresistor Coatings: The Effect of Film Morphology on Vapor Sensitivity. J Phys Chem C 112(32): 12507-12514.

Kane et al., (2011) Chemistry, physics, and engineering of electrically percolating arrays of nanoparticles: a mini review. J Mater Chem 21: 16846-16858.

Kim et al., (2011) Epidermal Electronics. Science 333(6044): 838-843.

Terrill et al., (1995) Monolayers in Three Dimensions: NMR, SAXS, Thermal, and Electron Hopping Studies of Alkanethiol Stabilized Gold Clusters. J Am Chem Soc 177(4): 12537-12548.

Tisch and Haick (2010) Arrays of chemisensitive monolayer-capped metallic nanoparticles for diagnostic breath testing. Reviews in Chemical Engineering 26(5-6): 171-179.

Ying et al., (2011) Design and experiment of flexible multi-functional tactile sensors for robot skin. CAAI Transactions on Intelligence Technology 3(1): 30-41.

* cited by examiner

Figure 5A  Figure 5B  Figure 5C
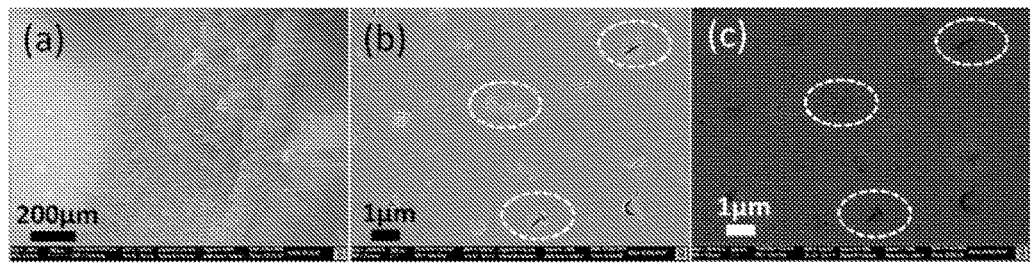
Figure 6A  Figure 6B  Figure 6C
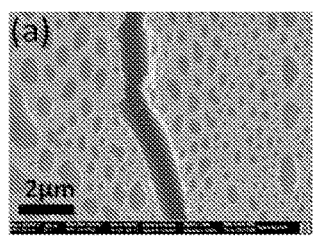 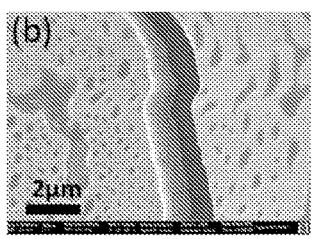 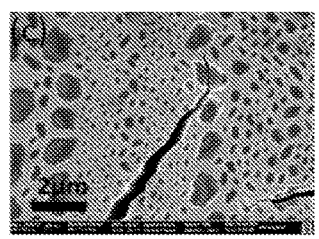
Figure 6D  Figure 6E  Figure 6F
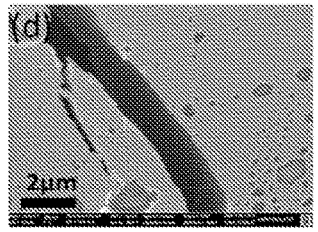 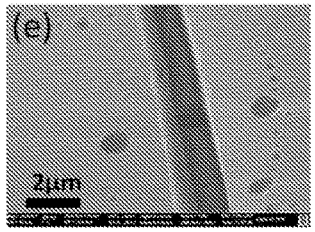 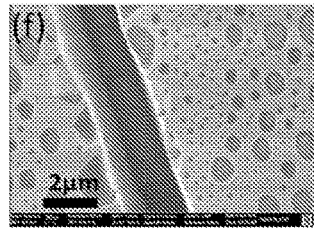
Figure 6G
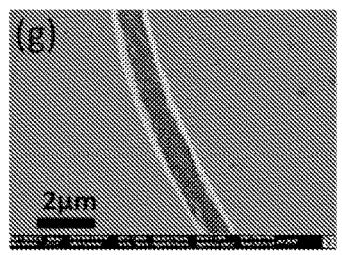

Figure 7A
Figure 7B
Figure 7C
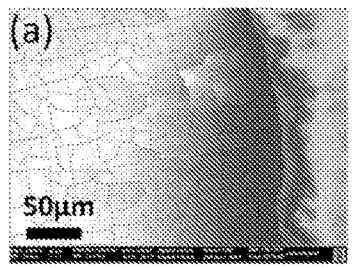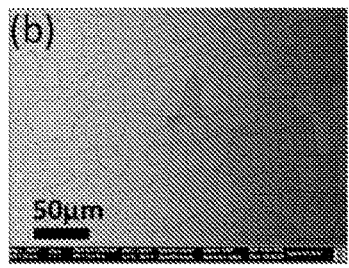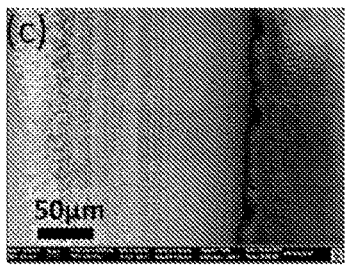
Figure 7D
Figure 7E
Figure 7F
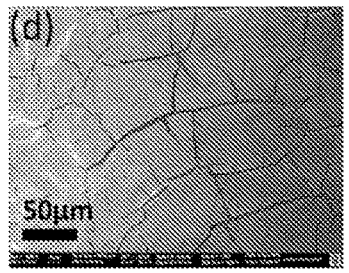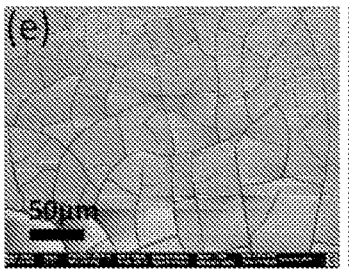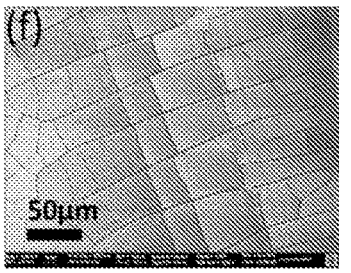
Figure 7G
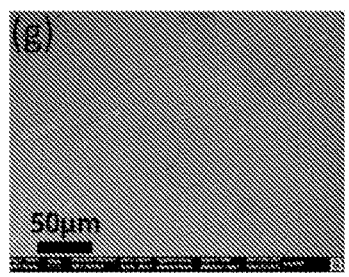

Figure 8A
Figure 8B
Figure 8C
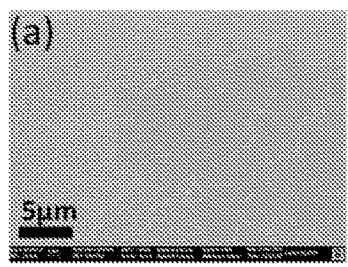
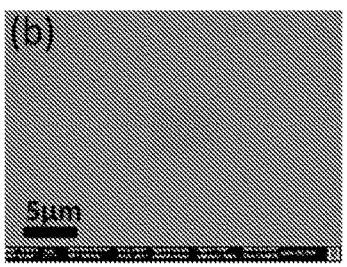
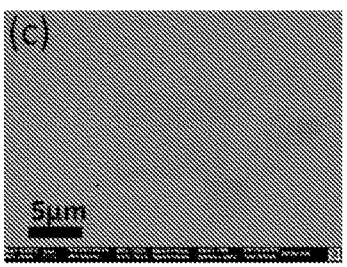
Figure 8D
Figure 8E
Figure 8F
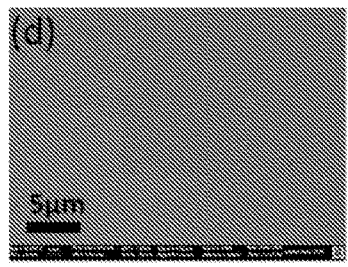
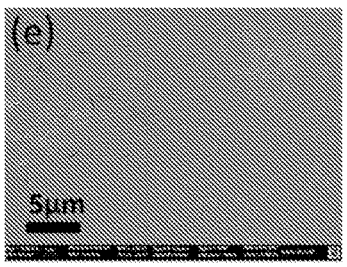
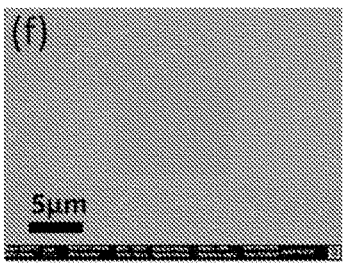
Figure 8G
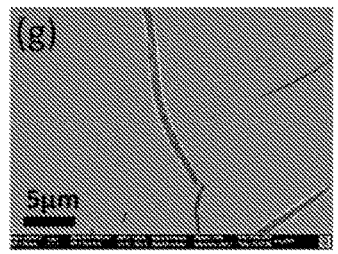

Figure 22A                    Figure 22B
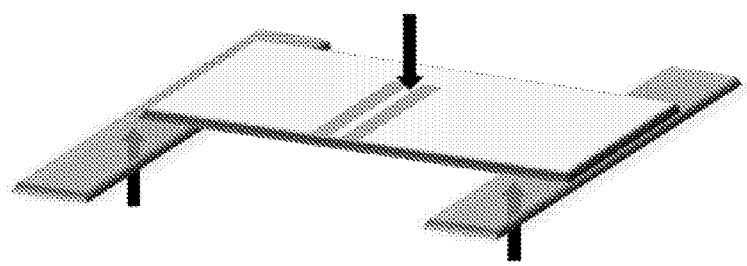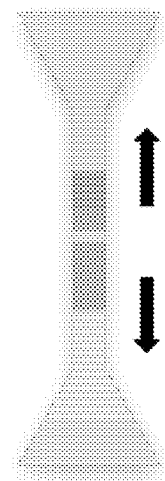
Figure 23
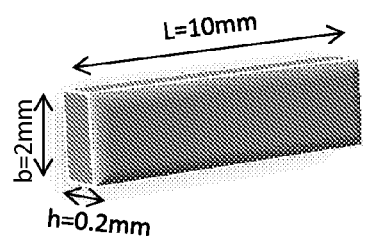

PLATFORM UNIT FOR COMBINED SENSING OF PRESSURE, TEMPERATURE AND HUMIDITY

FIELD OF THE INVENTION

The present invention is directed to a platform unit comprising a plurality of sensors comprising metallic nanoparticles capped with an organic coating for detecting pressure, temperature and humidity.

BACKGROUND OF THE INVENTION

Production of biomimetic artificial or electronic skin requires large-scale sensor arrays that are capable of sensing pressure, humidity and temperature with high resolution and low response times. These sensor arrays, designed to provide physical and chemical information of the environment can be utilized by a variety of applications such as medical prosthesis and robotics industries. For example, prosthetic limbs can be covered with artificial or electronic skin to provide the user with a sense of touch in the form of different pressure levels, and robotic limbs can be integrated with artificial or electronic skin surface of varying sensitivities to allow autonomous control for handling objects. Robotic surgeries, health monitoring and many other potential applications, can benefit from the use of artificial or electronic skin having varying sensitivities to pressure, temperature, and/or humidity conditions (Eltaib et al., Mechatronics 2003, 13, 1163-1177; Lee et al., Mechatronics 1999, 9, 1-31; and Dargahi et al., Int. J. Med. Rob. Comp. Ass. Surg. 2004, 1, 23-35).

Flexible sensors, originally designed as soft and rubbery components of hand-held consumer electronics and displays, are now being explored for use as ultrathin health-monitoring tapes that could be mounted onto the skin (Tiwana et al., Sens. Actuat. A 2012, 179, 17-31; and Rogers et al., PNAS, 2009, 106, 10875-10876). Low-power touch-sensitive platforms of flexible sensors that are based on nanowires, carbon nanotubes, nanoparticles, rubber dielectric layers, and organic field-effect transistors, have been successfully demonstrated (Takei et al., Nature Mater. 2010, 9, 821-826; Herrmann et al., Appl. Phys. Lett. 2007, 91, 183105; Siffalovic et al., Nanotech. 2010, 21, 385702; Vossmeyer et al., Adv. Funct. Mater. 2008, 18, 1611-1616; Maheshwari et al., Science, 2006, 312, 1501-1504; Mannsfeld et al., Nature Mater. 2010, 9, 859-864; Pang et al., Nature Mater. 2012, 11, 795-801; Matsuzaki et al., Sens. Actuat. A 2008, 148, 1-9; Lacour et al., Annual International Conference of the IEEE on Engineering in Medicine and Biology Society (EMBC), 2011, 8373-8376; Someya et al., PNAS 2004, 101, 9966-9970; Cosseddu et al., IEEE Elec. Dev. Lett. 2012, 33, 113-115; Joseph et al., J. Phys. Chem. C 2008, 112, 12507-12514; Boland, J. Nat. Mater. 2010, 9, 790-792; and Yu-Jen et al., IEEE Elec. Dev. Lett. 2011, 58, 910-917).

US 2011/0019373 discloses an arrangement for sensing ambient conditions in electric equipment and/or for sensing biometric variables of a user, preferably applied in mobile terminals.

US 2012/0062245 discloses an apparatus comprising: a dielectric structure including a plurality of elastomeric regions separated from one another by space regions, the elastomeric regions being configured and arranged, in response to pressure, to compress and thereby exhibit a changed effective dielectric constant corresponding to a state of compression of the elastomeric regions; and a sense circuit including a plurality of impedance-based sensors, each impedance-based sensor including a portion of the dielectric structure and configured and arranged to respond to the change in dielectric constant by providing an indication of the pressure applied to the dielectric structure adjacent each sensor.

In order to achieve wide range implementation of flexible sensors as artificial or electronic skin, several requirements have to be met. First, these sensors need to afford a wide dynamic range that will enable measuring both low pressures (i.e. 1-10 KPa) for small object manipulation as well as high pressures (i.e. 10-100 KPa) for manipulating heavy objects. Second, these sensors require the simultaneous measurement of pressure (touch), humidity, temperature and/or the presence of chemical compounds (Arregui et al., IEEE Sensors J. 2002, 2, 482-487; Cook et al., JPMC 2009, 5, 277-298; Shunfeng et al., IEEE Sensors J. 2012, 10, 856-862; Lopez-Higuera et al., J. Lightwave Tech. 2011, 29, 587-608; Konvalina et al., ACS Appl. Mater. Interf. 2012, 4, 317-325; Bay et al., J. S. Rob. Autom. Mag. IEEE 1995, 2, 36-43; and Wang et al., Langmuir 2010, 26, 618-632). Additional requirements include low-voltage/low power operation (typically below 5V), to be compatible with commonly used batteries of portable devices (Tsung-Ching et al., J. Disp. Tech. 2009, 5, 206-215). Finally, these sensors require easier, faster, and more cost-effective fabrication techniques to afford their wide application.

Layers of metallic-capped nanoparticles (MCNPs) on flexible substrates are potential candidates for a new generation of highly sensitive flexible sensors that meet these requirements (Herrmann et al., Appl. Phys. Lett. 2007, 91, 183105; Wang et al., Langmuir 2010, 26, 618-632; Wuelfing et al., J. Phys. Chem. B 2002, 106, 3139-3145; Haick, J. Phys. D 2007, 40, 7173-7186; Tisch et al., MRS Bull. 2010, 35, 797-803; Tisch et al., Rev. Chem. Eng. 2010, 26, 171-179; Vossmeyer et al., Adv. Funct. Mater. 2008, 18, 1611-1616; Farcau et al., J. Phys. Chem. C. 2011, 115, 14494-14499; and Farcau et al., ACS Nano 2011, 5, 7137-7143). The electrical properties of MCNP films exponentially depend on the inter-particle distance. Thus, deposition of the MCNPs on a flexible substrate allows modulating the resistance either by stretching or by bending the substrate. Geometry and mechanical properties of the substrate also affect the inter-particle separation. For example, metal-enhanced fluorescence, optical properties, and small-angle X-ray spectroscopy (SAXS) studies have shown that the nanoparticle separation depends on the substrate strain. Moreover, theoretical calculations have shown that the sensitivity of individual sensors to tactile load can be adjusted by controlling the thickness of the substrate.

WO 2009/066293, WO 2009/118739, WO 2010/079490, WO 2011/148371, WO 2012/023138, US 2012/0245434, US 2012/0245854, and US 2013/0034910 to some of the inventors of the present invention disclose apparatuses based on nanoparticle conductive cores capped with an organic coating for detecting volatile and non-volatile compounds, particularly for diagnosis of various diseases and disorders.

There remains an unmet need for the combined sensing of pressure, temperatures and humidity for multi-functional electronic or artificial skin applications.

SUMMARY OF THE INVENTION

The present invention provides a platform unit for detecting pressure, temperature and humidity using sensor technology which is based on metallic nanoparticles capped with an organic coating.

The present invention is based in part on the unexpected finding that sensors of metallic-capped nanoparticles (MC-NPs) can be used as pressure sensors when deposited on flexible substrates. These sensors allow the detection of a wide range of loads when using substrates having different geometrical and mechanical properties. Surprisingly, these sensors further provide highly sensitive temperature and humidity measurements thereby enabling the combined detection of physical and chemical environmental parameters. These results provide a new avenue to tailor the sensing properties of a modular matrix of MCNP sensors to afford their use as artificial or electronic skin.

According to a first aspect, the present invention provides a platform unit for detecting a parameter selected from the group consisting of pressure, temperature, humidity and a combination thereof, the platform unit comprising: a plurality of sensors comprising metallic nanoparticles capped with an organic coating, wherein the plurality of sensors comprise: at least one pressure sensor being deposited on a substantially flexible substrate, wherein the pressure sensor is configured to sense pressure applied thereon and to generate an electrical signal in response thereto, and at least one temperature or humidity sensor configured to exhibit a change in conformation of the metallic nanoparticles capped with an organic coating in response to a change in temperature or a change in humidity and generate an electrical signal in response thereto, thereby providing the detection of pressure, temperature, humidity or their combination. In one embodiment, the platform unit provides the concurrent detection of pressure, temperature and humidity.

In certain embodiments, the platform unit comprises at least three sensors comprising metallic nanoparticles capped with an organic coating, wherein the three sensors comprise a pressure sensor being deposited on a substantially flexible substrate, wherein the pressure sensor is configured to sense pressure applied thereon and to generate an electrical signal in response thereto, a temperature sensor configured to exhibit a change in conformation of the metallic nanoparticles capped with an organic coating in response to a change in temperature and generate an electrical signal in response thereto, and a humidity sensor configured to exhibit a change in conformation of the metallic nanoparticles capped with an organic coating in response to a change in humidity and generate an electrical signal in response thereto.

In some embodiments, the temperature and humidity sensors are configured to exhibit an independent change in conformation of the metallic nanoparticles capped with an organic coating in response to each of a change in temperature or a change in humidity.

In certain embodiments, the substantially flexible substrate comprises a polymer. In specific embodiments, the polymer is selected from the group consisting of polyimide, polyamide, polyimine, polyethylene, polyester, polydimethylsiloxane, polyvinyl chloride, and polystyrene. Each possibility represents a separate embodiment of the present invention. In other embodiments, the substantially flexible substrate comprises a silicon rubber. In yet other embodiments, the substantially flexible substrate comprises silicon dioxide. It will be recognized by one of skill in the art that by changing the material which forms the substantially flexible substrate, different load sensitivities of the pressure sensor can be obtained.

In other embodiments, the substantially flexible substrate is characterized by widths in the range of about 0.01-10 cm and thicknesses in the range of about 20-500 µm. It will be recognized by one of skill in the art that the geometrical parameters of the substantially flexible substrate can be used to control the load sensitivity of the pressure sensor.

In various embodiments, the pressure sensor is configured to generate an electrical signal which is proportional to the amount of deflection of the substantially flexible substrate. In other embodiments, the pressure sensor is configured as a strain gauge which translates the mechanical deflection into an electrical signal.

In further embodiments, the temperature or humidity sensors are deposited on a substantially flexible or substantially rigid substrate. Each possibility represents a separate embodiment of the present invention. In some embodiments, the substantially flexible substrate on which the temperature or humidity sensors are deposited comprises a polymer selected from the group consisting of polyimide, polyamide, polyimine, polyethylene, polyester, polydimethylsiloxane, polyvinyl chloride, and polystyrene. Each possibility represents a separate embodiment of the present invention. In yet other embodiments, the substantially flexible or rigid substrate on which the temperature or humidity sensors are deposited comprises silicon dioxide. In other embodiments, the substantially flexible substrate comprises a silicon rubber. In certain embodiments, the substantially rigid substrate is selected from the group consisting of metals, insulators, semiconductors, semimetals, and combinations thereof. Each possibility represents a separate embodiment of the present invention. In one embodiment, the substantially rigid substrate comprises silicon dioxide on a silicon wafer. In another embodiment, the substantially rigid substrate comprises a substantially rigid polymer. In yet another embodiment, the substantially rigid substrate comprises indium tin oxide.

In additional embodiments, the platform unit comprises a plurality of electrodes comprising an electrically conductive material, coupled to each sensor for measuring the signals generated by the sensors. In various embodiments, the distance between adjacent electrodes ranges between about 0.01 mm and about 5 mm. It will be recognized by one of skill in the art that the distance between adjacent electrodes which defines the sensing area can be used to control the sensitivity of the sensors to changes in load, temperature and/or humidity.

In some embodiments, each sensor in the platform unit is configured in a form selected from the group consisting of a capacitive sensor, a resistive sensor, a chemiresistive sensor, an impedance sensor, and a field effect transistor sensor. Each possibility represents a separate embodiment of the present invention. In exemplary embodiments, each sensor in the platform unit is configured as a chemiresistor.

In various embodiments, the platform unit further comprises a detection means comprising a device for measuring changes in resistance, conductance, alternating current (AC), frequency, capacitance, impedance, inductance, mobility, electrical potential, optical property or voltage threshold. Each possibility represents a separate embodiment of the present invention.

In yet other embodiments, the metallic nanoparticles are selected from the group consisting of Au, Ag, Ni, Co, Pt, Pd, Cu, Al, and combinations thereof. Each possibility represents a separate embodiment of the present invention. In additional embodiments, the metallic nanoparticles are metallic alloys selected from the group consisting of Au/Ag, Au/Cu, Au/Ag/Cu, Au/Pt, Au/Pd, Au/Ag/Cu/Pd, Pt/Rh, Ni/Co, and Pt/Ni/Fe. Each possibility represents a separate embodiment of the present invention. In an exemplary embodiment, the metallic nanoparticles are gold (Au) nanoparticles.

In other embodiments, the metallic nanoparticles have a geometry selected from the group consisting of a cubic, a spherical, and a spheroidal geometry. Each possibility represents a separate embodiment of the present invention.

In further embodiments, the organic coating comprises compounds selected from the group consisting of alkylthiols, arylthiols, alkylarylthiols, alkylthiolates, ω-functionalized alkanethiolates, arenethiolates, (γ-mercaptopropyl)trimethyloxysilane, dialkyl disulfides and combinations and derivatives thereof. Each possibility represents a separate embodiment of the present invention. In an exemplary embodiment, the organic coating is 2-nitro-4-trifluoro-methylbenzenethiol. In another exemplary embodiment, the organic coating is 3-ethoxythiophenol. In yet another exemplary embodiment, the organic coating is decanethiol. In further exemplary embodiments, the organic coating is dodecylamine. In various embodiments, the organic coating is characterized by a thickness ranging from about 1 nm to about 500 nm.

In several embodiments, the platform unit further comprises a film, wherein the film is configured to block at least one sensor from generating a signal in response to a change in humidity. In some embodiments, the film comprises a resin selected from the group consisting of an epoxy resin, a silicon resin, a polyamide resin, a polyimide resin, a poly(p-xylylene) resin and a combination thereof. Each possibility represents a separate embodiment of the present invention. In additional embodiments, the film thickness ranges from about 1 μm to about 1000 μm.

According to one embodiment, the platform unit further provides the detection of a volatile organic compound (VOC) of interest using an analyte sensor, wherein the analyte sensor is configured to sense an analyte adsorbed thereon and to generate an electrical signal in response thereto. In another embodiment, the platform unit further provides the detection of a volatile organic compound indicative of a disease in a subject. In yet another embodiment, the platform unit further comprises a film, wherein the film is configured to block at least one sensor (e.g. the temperature, humidity and/or pressure sensor) from generating a signal in response to a volatile organic compound (VOC) of interest.

In various embodiments, the platform unit comprises at least three sensors comprising metallic nanoparticles capped with similar or different organic coatings, wherein the three sensors comprise a pressure sensor being deposited on a substantially flexible substrate, wherein the pressure sensor is configured to sense pressure applied thereon and to generate an electrical signal in response thereto, a temperature sensor configured to exhibit a change in conformation of the metallic nanoparticles capped with an organic coating in response to a change in temperature and generate an electrical signal in response thereto, and a humidity sensor configured to exhibit a change in conformation of the metallic nanoparticles capped with an organic coating in response to a change in humidity and generate an electrical signal in response thereto.

In one embodiment, the platform unit comprises at least three sensors comprising metallic nanoparticles capped with similar or different organic coating, wherein the three sensors comprise a pressure sensor being deposited on a substantially flexible substrate, wherein the pressure sensor is configured to sense pressure applied thereon and to generate an electrical signal in response thereto, a temperature sensor being deposited on a substantially rigid substrate, wherein the temperature sensor is configured to exhibit a change in conformation of the metallic nanoparticles capped with an organic coating in response to a change in temperature and generate an electrical signal in response thereto, and a humidity sensor being deposited on a substantially rigid substrate, wherein the humidity sensor is configured to exhibit a change in conformation of the metallic nanoparticles capped with an organic coating in response to a change in humidity and generate an electrical signal in response thereto. In exemplary embodiments, the pressure sensor and the temperature sensor comprise organic coating having low sensitivity to humidity (i.e. water vapor). In another exemplary embodiment, the pressure sensor and the temperature sensor comprise a film which is configured to block the sensors from generating a signal in response to a change in humidity.

In other embodiments, at least one sensor in the platform unit comprises dual sensing sensitivities. In one exemplary embodiment, the sensor comprising dual sensing sensitivities is a temperature and humidity sensor being deposited on a substantially flexible or rigid substrate, wherein the sensor is configured to exhibit a change in conformation of the metallic nanoparticles capped with an organic coating in response to a change in temperature and a change in humidity and generate a plurality of different electrical signals in response thereto. In another exemplary embodiments, the sensor comprising dual sensing sensitivities is a pressure and humidity sensor being deposited on a substantially flexible substrate, wherein the sensor is configured to sense pressure applied thereon and to generate an electrical signal in response thereto and is further configured to exhibit a change in conformation of the metallic nanoparticles capped with an organic coating in response to a change in humidity and generate an electrical signal in response thereto. In yet another exemplary embodiment, the sensor comprising dual sensing sensitivities is a pressure and temperature sensor being deposited on a substantially flexible substrate, wherein the sensor is configured to sense pressure applied thereon and to generate an electrical signal in response thereto and is further configured to exhibit a change in conformation of the metallic nanoparticles capped with an organic coating in response to a change in temperature and generate an electrical signal in response thereto.

In other exemplary embodiments, the platform unit of the present invention comprising two sensors, wherein one sensor is a dual pressure and humidity sensor being deposited on a substantially flexible substrate, and the other sensor is a dual pressure and temperature sensor being deposited on a substantially flexible substrate.

One of skill in the art readily understands that a signal which corresponds to changes in each of load, temperature and/or humidity can be extracted from a dual sensor's signal using various pre-measurement calibrations and/or post-measurement calculations using algorithms known by those of skill in the art.

In some embodiments, the humidity sensor comprises continuous and discontinuous regions of metallic nanoparticles capped with an organic coating. In one embodiment, the discontinuous regions comprise voids ranging in size from about 10 nm to about 500 nm. In another embodiment, the discontinuous regions comprise between about 3% and about 90% voids.

According to additional embodiments, the platform unit of the present invention is integrated on electronic or artificial skin surface.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

(FIG. 1A) $\Delta R/R_b$ of NTMBT-MCNP-based sensor in response to changing the temperatures from 23° C. to 39° C. Inset: a magnification of the temperatures region of 35-39° C. (FIG. 1B) $\Delta R/R_b$ of NTMBT-MCNP-based sensor in response to various relative humidity levels.

(FIG. 3A) A schematic illustration of the relaxed substrate with ETP-MCNPs film. (FIG. 3B) A schematic illustration of the bent substrate with ETP-MCNPs film and the effect of the bending on the ETP-MCNPs spacing. (FIGS. 3C-3E): Photographs of the device on PET in (FIG. 3C) relaxed state, (FIG. 3D) upward bent, and (FIG. 3E) downward bent. The distance between the electrodes is about 1 mm. (FIG. 3F) $\Delta R/R_b$ of ETP-MCNP-based sensor on PET in response to stretching during three-point bending measurements with loading (■) and unloading (○) of stress. (FIG. 3G) $\Delta R/R_b$ of ETP-MCNP-based sensor on PET in response to compression during three-point bending measurements with loading (■) and unloading (○) of stress. The dashed lines represent linear fits to the curves, with $R^2$ in the range of 0.996-0.999 for all 4 curves. The sensitivity limit is down to tens of Pa, with 40 Pa being the limit of detection for the PET substrate. (FIG. 3H) $\Delta R/R_b$ of ETP-MCNP sensor (thick line) to load and unload (thin line) vs. time. (FIG. 3I) $\Delta R/R_b$ vs. time in response to 12 cycles of load (0.75 gr) and unload.

(FIG. 4C) Resistance shifts of the DT-MCNP-based sensor as a result of bending the surface. The load onset is indicated in grams. (FIG. 4D) Repeatability of sensor's response to applied stress of ~250 Pa (~0.5 gram).

FIGS. 5A-5C: FE-HRSEM images of a layer of ETP-MCNP which was drop casted on Mylar® 36 substrate. (FIG. 5A) An image of the drop margins using SE detector; (FIG. 5B) An image of the center of the drop using SE detector. (FIG. 5C) An image of the center of the drop using BSE detector. The dashed white circles in (FIGS. 5B and 5C) mark cracks as deep as the layer-substrate interface.

FIGS. 6A-6G: High magnification FE-HRSEM images of the margins of ETP-MCGNP drop casted layer on (FIG. 6A) Kapton® 50, (FIG. 6B) Kapton® 127, (FIG. 6C) PET 125, (FIG. 6D) Kapton® b. 131, (FIG. 6E) Mylar® 36, (FIG. 6F) Mylar® 50 and (FIG. 6G) PVC 200 using SE detector.

FIGS. 7A-7G: FE-HRSEM images of the margins of ETP-MCGNP drop casted layer on (FIG. 7A) Kapton® 50, (FIG. 7B) Kapton® 127, (FIG. 7C) PET 125, (FIG. 7D) Kapton® b. 131, (FIG. 7E) Mylar® 36, (FIG. 7F) Mylar® 50 and (FIG. 7G) PVC 200 using SE detector.

FIGS. 8A-8G: Low magnification FE-HRSEM images of ETP-MCNP drop-casted layer on: (FIG. 8A) Kapton® 50, (FIG. 8B) Kapton® 127, (FIG. 8C) PET 125, (FIG. 8D) Kapton® b. 131, (FIG. 8E) Mylar® 36, (FIG. 8F) Mylar® 50, and (FIG. 8G) PVC 200, using SE detector.

(FIG. 9A) $\Delta R/R_b$ of ETP-MCNP films on different flexible substrates (Mylar® 50: ♦; Mylar® 36: ▽; PET 125: ○; Kapton® b. 131: ▲; Kapton® 127: □; Kapton 50: ★; and PVC 200: ◁) vs. load, as measured by three-point bending tests. (FIG. 9B) The load sensitivity of the sensors having substrates with different properties, as a function of the Young's modulus, geometrical property, and moment of inertia.

FIGS. 10A-10B: $\Delta R/R_b$ vs. load (bottom x-axis) and strain (upper x-axis) for: (FIG. 10A) ETP-MCNP film deposited on Mylar®36 (load sensitivity=0.31) subjected to loads of 200 mg-1 gr; and (FIG. 10B) ETP-MCNP film deposited on PET 125 (load sensitivity=0.01) subjected to loads of 200 mg-10 gr.

(FIG. 11A) $\Delta R/R_b$ of ETP-MCNP sensor (thick line) to load and unload (thin line) vs. time. (FIG. 11B) The load sensitivity of the sensors produced on substrates with different elastic properties, as a function of the Young's modulus and the substrate thickness. The error bars are the standard deviation of 3 similar sensors and the dashed line represents the linear trend of the results.

(FIG. 12A) The change in load sensitivity (left y-axis) and sensors' resistance (right y-axis) using sensors fabricated on electrodes with 0.5 mm, 1 mm and 3 mm spacing. The error bars are the standard deviation of 3 tested sensors for specific electrode spacing. (FIG. 12B) The change in load sensitivity for the same electrode structure and substrate when changing the width of the substrate. The error bars are the standard deviation of 3 repetitions on the same sensor with specific dimensions. (FIG. 12C) The change in load sensitivity for different MCNP ligands (NT-MBT: ○; and ETP: ✻). The dashed lines represent linear fits to the curves and the error bars are standard deviation of 3-5 sensors.

(FIG. 14A) Change in the baseline resistance of ETP-MCNP/Kapton®127 sensors vs. the number of bending cycles. (FIG. 14B) $\Delta R/R_b$ vs. load after 1 (□), 5,000 (△), and 10,000 (○) bending cycles.

(FIG. 15A) $\Delta R/R_b$ of ETP-MCNP-based sensor on a PET substrate upon changes in temperature from 23° C. to 39° C. Inset: RH fluctuations during the experiment. (FIG. 15B) $\Delta R/R_b$ of ETP-MCNP-based sensor to various RH levels. The dashed line represents a linear fit with $R^2=0.98$. The error bars are the standard deviations of tens of measurement points of the response at a specific RH level. Inset: Temperature fluctuations during the experiment.

(FIG. 16A) Morse code alphabet and digits. (FIG. 16B) Encoding "LNBD" on ETP-MCNP-based sensor with a 36 μm thick Mylar® substrate. (FIG. 16C) Encoding "SOS" on ETP-MCNP-based sensor with a 125 μm thick PET substrate. The pressure was applied using a finger (with an estimated pressure of approximately 1 KPa).

(FIG. 18A) relative humidity, and (FIG. 18B) temperature. $\Delta R/R_b$ of ETP- MCNP sensor on a silicon dioxide substrate vs. (FIG. 18C) relative humidity, and (FIG. 18D) temperature.

(FIG. 19A) The resistance of flexible ETP-MCNP sensor on PET substrate as a function of the temperature at 3% RH (▲) and at 20% RH (○). The plots on the right show the RH fluctuations when changing the temperatures. (FIG. 19B) The resistance of flexible ETP-MCNP sensor on PET substrate as a function of % RH at 21° C. (□), 25° C. (x) and 30° C. (●). The plots on the right describe the temperature fluctuations when changing the RH conditions.

(FIG. 21A) A schematic illustration of an exemplary platform of the present invention using a Kapton® substrate and gold electrodes. (FIG. 21B) Different planes representing changes in resistance of S1 and S2 when exposing the sensors to changing conditions of temperature and relative humidity. (FIG. 21C) $\Delta R/R_b$ of S3 to applied pressure.

FIGS. 22A-22B: (FIG. 22A) A schematic illustration of the three-point bending setup. The points marked by the bottom arrows represent the static lean beams on which the flexible substrate rests. The upper arrow represents the location at which strain is applied. (FIG. 22B) A schematic illustration of the stretching setup. The substrate is in a "dog bone" morphology were the grips are attached to the wider part of the sample. The arrows represent the direction of the applied strain.

FIG. 23: A schematic illustration of a three-point bending sample dimensions.

DETAILED DESCRIPTION OF THE INVENTION

Figure 1A:
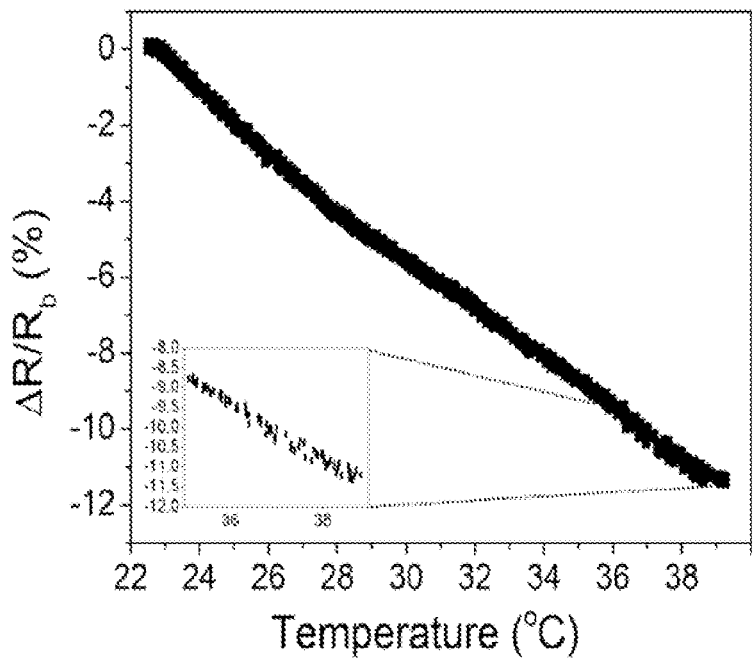
FIGS. 1A-1B.

The present invention provides a modular matrix or platform unit for the concurrent detection of pressure, temperature and humidity. In particular, provided herein is a platform comprising MCNP-based sensors which operate at low-power (<0.5V) for multi-functional artificial or electronic skin applications.

The present invention is based in part on the unexpected finding that MCNP-based flexible sensors can possess repeatable measurements of elastic deformation with load sensitivity ≤0.24 gr. In addition, it is further disclosed that the same sensor technology can be used for sensing environmental conditions with excellent sensitivities for measuring changes in temperature (below 1° C.) and humidity (below 1% RH). It was not previously realized that it is possible to use MCNP-based sensors for concurrent detection of pressure, temperature and humidity on a single platform unit. The ability to detect pressure, temperature and humidity using the same sensor technology integrated on a single platform unit provides a significant advantages over the prior art. The MCNP-based sensors provide repeatable responses even after many bending cycles which render them advantageous for long-term use. Another advantage to the present invention stems from the ability to manufacture micro-scale sensors having high spatial resolution in mass production, thereby enabling their integration in an artificial or electronic skin in well-defined and controllable locations.

In order to achieve independent sensitivities of individual sensors to a single desirable parameter, the following fabrication modulations can be applied:

(i) by using substrates having varying flexibilities and geometric characteristics. For example, by using substantially flexible substrates, the sensor generates an electrical signal mainly attributed to the applied force and not to changes in temperature and humidity. Similarly, by using substantially rigid non-stretching substrates, the sensor generates an electrical signal mainly attributed to changes in temperature and/or humidity and not to pressure.

(ii) by using different organic coatings of the metallic nanoparticles. For example, by using a short di-thiol linker as the capping organic coating, the responses of the sensor to gaseous analytes (including water vapors) can be substantially suppressed. By using a long linker as the capping organic coating, adsorption of various gases can be obtained thereby affording a measurable electrical signal in response to the swelling of the assembly of capped nanoparticles.

(iii) by adding a thin (50 μm thick) polymer film, as the top-cover of the sensor. For example, the addition of a top cover can substantially suppress the sensing of humidity and/or volatile organic compounds. Thus, it is contemplated that a thin top-cover film would restrict water vapors from interacting with the metallic nanoparticles capped with an organic coating. The top cover should be thin and possess good heat conduction and low heat capacitance characteristics to assure fast and accurate responses to changes in temperature and/or pressure.

(iv) by modifying the deposition parameters. For example, by using the layer-by-layer deposition technique (Makishima et al., J. Non-Cryst. Sol. 1973, 12, 35-45), control over sensing sensitivities to various analytes can be obtained.

(v) by depositing the NPs at different humidity levels. Thus, it is contemplated that a sensor comprising a film of MCNP which has discontinuous regions provides positive responses upon exposure to various analytes, but negative responses upon exposure to water vapor. By changing the amount of voids in the discontinuous regions, it is possible to control the sensitivity to humidity (water vapors).

(vi) by using pre-measurement calibrations and/or post-measurement algorithmic compensation, an extraction of the data affected by a single parameter (e.g., only temperature) or a plurality of parameters (temperature, humidity and load or strain) can be obtained. For example, two sensors with low sensitivity to load or strain can afford the sensing of changes in temperature and humidity each, while a third flexible sensor affords the sensing of temperature, humidity and load or strain. Post-measurement algorithms can be used to compensate the signals produced by changes in temperature and humidity of the third flexible sensor and enable the extraction or isolation of the signal generated by applied load or strain. In another example, two sensors may sense temperature and humidity simultaneously, having different sensitivities towards each parameter. Then, post-measurement algorithms can be used to calculate the temperature and the relative humidity in an injective manner.

The MCNP-based sensing platform unit of the present invention is particularly suitable for use in artificial or electronic skin technology. The platform unit of the present invention obviates the need for complex integration processes of substantially different devices, each device being sensitive to humidity, temperature, or pressure. The MCNP-based sensing platform unit of the present invention is compatible with cost-effective mass production using various deposition techniques (e.g. spray coating). An additional advantage stems from the wide range of pressures that can be detected and measured by the pressure sensors, which can be achieved by depositing MCNPs on different substrates having various mechanical properties and geometrical characteristic. Moreover, the use of MCNPs pressure sensors on flexible substrates afforded the measurement of very low pressures that have never been detected by the hitherto known pressure sensors (Maenosono et al., J. of Nanopart. Res. 2003, 5, 5-15). Another advantage of the MCNP-based sensors is their ability to operate at low voltage of ~0.5V, whereas the hitherto known skin technologies require operation at 5V or more. Such low voltage demands facilitate the integration of the technology presented herein using mobile batteries.

The present invention therefore provides MCNP-based sensing platform unit with excellent temperature and humidity sensitivities which enables the sensing of environmental conditions. The MCNP-based sensing platform unit of the present invention also provides excellent sensitivity to strain which enables its use as "touch" sensors. The MCNP-based sensing platform unit can be integrated in artificial or electronic skin applications.

According to the principles of the present invention, the platform unit provides the detection of pressure, temperature, and/or humidity. In some embodiments, the platform unit provides the concurrent detection of pressure, temperature, and humidity. The platform unit comprises a plurality of sensors, each sensor comprises a plurality of metallic nanoparticles capped with an organic coating. In certain embodiments, each sensor comprises a plurality of metallic nanoparticles capped with different organic coatings. Suitable metallic nanoparticles within the scope of the present invention include, but are not limited to Au, Ag, Ni, Co, Pt, Pd, Cu, Al, and combinations thereof, including metallic alloys such as, but not limited to Au/Ag, Au/Cu, Au/Ag/Cu, Au/Pt, Au/Pd, Au/Ag/Cu/Pd, Pt/Rh, Ni/Co, and Pt/Ni/Fe. Each possibility represents a separate embodiment of the present invention.

The organic coating of the metallic nanoparticles comprises a monolayer or multilayers of organic molecules. Suitable coating includes, but is not limited to alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, ω-functionalized alkanethiolates, arenethiolates, (γ-mercaptopropyl)tri-methyloxysilane, dialkyl disulfides and combinations thereof. Each possibility represents a separate embodiment of the present invention. Exemplary organic coating includes, but is not limited to 2-nitro-4-trifluoro-methylbenzenethiol, 3-ethoxythiophenol, dodecylamine, and decanethiol. Each possibility represents a separate embodiment of the present invention. In various embodiments, the organic coating is characterized by a thickness ranging from about 1 nm to about 500 nm.

Sensors comprising metallic nanoparticles capped with an organic coating can be synthesized as is known in the art, for example using the two-phase method (Brust et al., J. Chem. Soc. Chem. Commun., 1994, 7, 801) with some modifications (Hostetler et al., Langmuir 1998, 14, 17). In a non-limiting example, $AuCl_4^-$ is transferred from aqueous $HAuCl_4 \cdot xH_2O$ solution to a toluene solution by the phase-transfer reagent TOAB. After isolating the organic phase, excess thiols are added to the solution. The mole ratio of thiol:$HAuCl_4 \cdot xH_2O$ can vary between 1:1 and 10:1, depending on the thiol used. This is performed in order to prepare mono-disperse solution of gold nanoparticles in an average size of about 3-6 nm. Exemplary procedures include, but are not limited to thiol:Au mole ratios of 10:1 and 1:1 for dodecanethiol and butanethiol-capped gold nanoparticles, respectively at an average size of about 5 nm. After vigorous stirring of the solution, aqueous solution of the reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with e.g. 2-mercaptobenzimidazole can be synthesized by the ligand-exchange method from pre-prepared hexanethiol-capped gold nanoparticles. In a typical reaction, excess of thiol, 2-mercaptobenzimidazole, is added to a solution of hexanethiol-capped gold nanoparticles in toluene. The solution is kept under constant stirring for a few days in order to allow as much ligand conversion as possible. The nanoparticles are purified from free-thiol ligands by repeated extractions. The metallic nanoparticles may have any desirable geometry including, but not limited to a cubic, a spherical, and a spheroidal geometry. Each possibility represents a separate embodiment of the present invention.

In some embodiments, the plurality of sensors comprise at least one pressure sensor which is configured to sense pressure applied thereon and to generate an electrical signal in response thereto. According to the principles of the present invention, the pressure sensor is fabricated on a substantially flexible substrate. The term "a substantially flexible substrate" as used herein refers to a substrate which is configured to elastically deform in response to pressure, wherein said deformation is proportional to the amount of applied pressure. In certain embodiments, the deformation of the substrate generates a change in conformation of the metallic nanoparticles capped with an organic coating. The change in conformation or structural displacement of the metallic nanoparticles capped with an organic coating generates an electrical signal which is proportional to the amount of applied pressure. In other embodiments, the pressure sensor is configured as a strain gauge which translates the mechanical deflection into an electrical signal.

Suitable substantially flexible substrates include stretchable substrates as is known in the art. Exemplary substrates include, but are not limited to polymers which may be polyimide (e.g. Kapton®), polyamide, polyimine (e.g. polyethylenimine), polyethylene, polyester (e.g. Mylar®, polyethylene terephthalate, polyethylene naphthalate), polydimethylsiloxane, polyvinyl chloride (PVC), polystyrene and the like. Each possibility represents a separate embodiment of the present invention. In one embodiment, the substrate comprises silicon dioxide. In another embodiment, the substrate comprises Si rubber. By modifying the material which forms the substantially flexible substrate from a material having high Young's modulus to a material having low Young's modulus, a change in load sensitivities can be obtained. It is thus contemplated that the substantially flexible substrate enables to control the load sensitivity of the pressure sensor.

The substantially flexible substrate can have any desirable geometry. In rectangular geometries, the width of the substantially flexible substrate ranges between about 0.01-10 cm. The thickness of the substrate can further be tuned, typically in the range of about 20-500 μm. The present invention provides the modulation of load sensitivities by changing the width of the sensors' substrate. In addition, the present invention provides the modulation of the gauge factor by adjusting the substrate thickness. Thus, it is contemplated that by modifying the geometrical characteristics of the substrate, desirable load sensitivity and strain gauge factor can be obtained.

The platform unit of the present invention further comprises at least one temperature and/or humidity sensor configured to exhibit a change in conformation of the metallic nanoparticles capped with an organic coating in response to a change in temperature and/or a change in humidity. This change in conformation is then translated into an electrical signal generated in response. Accordingly, the electrical signal is proportional to the change in humidity and/or change in temperature.

In some embodiments, the temperature and/or humidity sensor is fabricated on a substantially rigid or substantially flexible substrate as described herein. Typically, the temperature and/or humidity sensor is fabricated on a substantially rigid substrate. Suitable substantially rigid substrates within the scope of the present invention include, but are not limited to metals, insulators, semiconductors, semimetals, and combinations thereof. Each possibility represents a separate embodiment of the present invention. In exemplary embodiments, the substantially rigid substrate comprises silicon dioxide on a silicon wafer. In another exemplary embodiment, the substantially rigid substrate comprises a substantially rigid polymer. In yet another exemplary embodiment, the substantially rigid substrate comprises indium tin oxide.

In various embodiments, the pressure and/or temperature sensors of the present invention are coated with a film. According to the principles of the present invention, the film is configured to block the pressure and/or temperature sensors from generating a signal in response to a change in humidity. Non-limiting examples of films within the scope of the present invention include epoxy resin films, silicon resin films, polyamide resin films (e.g. nylon and aramid resins), polyimide resin films, poly(p-xylylene) resin films (e.g. Parylenes®) and a combination thereof. Each possibility represents a separate embodiment of the present invention. Typically, the film which is configured to block the pressure and/or temperature sensors from generating a signal in response to a change in humidity has thickness in the range of about 1-1000 μm.

According to certain aspects and embodiments, the platform unit comprises at least three sensors comprising metallic nanoparticles capped with an organic coating as follows:

(i) a pressure sensor being deposited on a substantially flexible substrate, wherein the pressure sensor is configured to sense pressure applied thereon and to generate an electrical signal in response thereto;

(ii) a temperature sensor being deposited on a substantially rigid substrate, wherein the temperature sensor is configured to exhibit a change in conformation of the metallic nanoparticles capped with an organic coating in response to a change in temperature and generate an electrical signal in response thereto; and (iii) a humidity sensor being deposited on a substantially rigid substrate, wherein the humidity sensor is configured to exhibit a change in conformation of the metallic nanoparticles capped with an organic coating in response to a change in humidity and generate an electrical signal in response thereto.

In some embodiments, the temperature and humidity sensors are configured to exhibit an independent change in conformation of the metallic nanoparticles capped with an organic coating in response to each of a change in temperature or a change in humidity.

According to certain aspects and embodiments, the humidity sensor comprises continuous and discontinuous regions of conductive metallic nanoparticles capped with an organic coating. In one embodiment, the discontinuous regions comprise voids ranging in size from about 10 nm to about 500 nm, wherein the percentage of voids ranges between about 3% and about 90%.

In certain embodiments, the platform unit comprises a plurality of conducting elements (e.g. electrodes) which are coupled to each sensor, thereby enabling the measurement of the signals generated by the sensors. The conducting elements may include a source and a drain electrode separated from one another by a source-drain gap. The conducting elements may further comprise a gate electrode wherein the electrical signal may be indicative of a certain property of the capped nanoparticles (e.g. a change in conformation of the capped nanoparticles) under the influence of a gate voltage.

The conducing elements may comprise metals such as Au, Ag or Pt electrodes and may further be connected by interconnecting wiring. The distance between adjacent electrodes defines the sensing area. Accordingly, different configurations of the electrodes in the platform unit may be fabricated as is known in the art. Typically, the distance between adjacent electrodes in each sensor ranges between about 0.01-5 mm. In some embodiments, the metallic nanoparticles are casted on a plurality of interdigitated electrodes on a substantially flexible or rigid substrate.

The electrical signal which is generated by the pressure, temperature or humidity sensors may comprise, according to the principles of the present invention any one or more of conductivity, resistance, impedance, capacitance, inductance, or optical properties of the sensors. In some embodiments, the electrical signal is produced by the swelling of the assembly of capped nanoparticles in response to changes in pressure, temperature or humidity. As used herein, the term "swelling" refers to an increase of the average inter-particle distance in the assembly of capped nanoparticles. In other embodiments, the electrical signal is produced by the aggregation of the assembly of capped nanoparticles in response to changes in pressure, temperature or humidity. As used herein, the term "aggregation" refers to a decrease of the average inter-particle distance in the assembly of capped nanoparticles.

The sensor signal can be detected by a detection means. Suitable detection means include devices which are susceptible to a change in any one or more of resistance, conductance, alternating current (AC), frequency, capacitance, impedance, inductance, mobility, electrical potential, optical property and voltage threshold. Each possibility represents a separate embodiment of the present invention. In additional embodiments, the detection means includes devices which are susceptible to swelling or aggregation of capped nanoparticles as well as devices which are susceptible to a change in any one or more of optical signal (detected by e.g. spectroscopic ellipsometry), florescence, chemiluminsence, photophorescence, bending, surface acoustic wave, piezoelectricity and the like. Each possibility represents a separate embodiment of the present invention. The measured electrical signals can be displayed on a display or transmitted to a host computer.

The sensors of the present invention can be configured as any one of the various types of electronic devices, including, but not limited to capacitive sensors, resistive sensors, chemiresistive sensors, impedance sensors, field effect transistor sensors, and the like, or combinations thereof. Each possibility represents a separate embodiment of the present invention. In a non-limiting example, the sensors of the present invention are configured as chemiresistive sensors (i.e. chemiresistors). In one embodiment, the sensors of the present invention are not configured as impedance sensors.

Sensors comprising a plurality of metallic nanoparticles capped with an organic coating can be formed on flexible or rigid substrates using a variety of techniques well known in the art. Exemplary techniques include, but are not limited to, (i) Random deposition from solution by drop casting, spin coating, spray coating and other similar techniques. Each possibility represents a separate embodiment of the present invention.

(ii) Field-enhanced or molecular-interaction-induced deposition from solution. Each possibility represents a separate embodiment of the present invention.

(iii) Langmuir-Blodgett or Langmuir-Schaefer techniques. Each possibility represents a separate embodiment of the present invention.

(iv) Soft lithographic techniques, such as micro-contact printing (mCP), replica molding, micro-molding in capillaries (MIMIC), and micro-transfer molding (mTM). Each possibility represents a separate embodiment of the present invention.

(v) Various combinations of Langmuir-Blodgett or Langmuir-Schaefer methods with soft lithographic techniques. Each possibility represents a separate embodiment of the present invention.

(vi) Printing on solid-state or flexible substrates using an inject printer designated for printed electronics.

The present invention further encompasses sensors having dual sensing sensitivities, such as a dual temperature and pressure sensor, a dual temperature and humidity sensor, and/or a dual pressure and humidity sensor. Each possibility represents a separate embodiment of the present invention. A non-limiting example of a platform unit which comprises dual sensors includes a platform unit comprising three sensors, wherein two sensors are dual temperature and humidity sensors being deposited on a substantially flexible substrate, and a third pressure sensor being deposited on a substantially flexible substrate. It is contemplated that the choice of substrate is used to alter the sensitivity of the sensors to changes in load, temperature and/or humidity. An additional non-limiting example of a platform unit which comprises dual sensors includes a platform unit comprising two sensors, wherein one sensor is a dual pressure and humidity sensor being deposited on a substantially flexible substrate, and the other sensor is a pressure and temperature sensor being deposited on a substantially flexible substrate. One of skill in the art readily understands that a signal generated by each parameter (temperature, humidity or pressure) is extracted using pre-measurement calibration, post-measurement calculation or a combination thereof.

The arrangement of the plurality of sensors in the platform unit can be performed as is known in the art. Non-limiting arrangement includes a matrix of sensors (rows and columns) comprising a plurality of sensors, for example between 2 and 20 sensors, wherein each sensor independently generates an electrical signal in response to pressure, temperature and/or humidity. Each sensor comprises metallic nanoparticles capped with a different or similar organic coating and a different or similar substrate.

According to certain aspects and embodiments, the sensors of the present invention are coated with a film. In some embodiments, the film provides the protection of the metallic nanoparticles capped with an organic coating from physical damage, scratching and oxidation. The coating can be performed by processes well known in the art such as, but not limited to, spin coating and the like. The film could be permeable to water or not, depending on the required application. The film could conduct heat or isolate the sensor from external temperature changes. In some embodiments, the film comprises polycyclic aromatic hydrocarbons (PAHs). In other embodiments, the film comprises carbon coatings, nitrogenated carbon coatings, thermoplastic resins, silicate coatings or any other suitable coating known in the art. Typically, the film possesses a thickness which ranges from about 0.001 to about 10 μm.

According to various aspects and embodiments, the platform unit further provides the detection of a volatile organic compound (an analyte) using an analyte sensor, wherein the analyte sensor is configured to sense an analyte adsorbed thereon and to generate an electrical signal in response thereto. Thus, it is contemplated that the platform unit would further provide the detection of the presence and concentration of volatile organic compounds in the surrounding environment. In some embodiments, the volatile organic compounds are biomarkers indicative of a disease or disorder in a subject.

The platform unit of the present invention may be used for artificial and/or electronic skin applications which require the production of large-scale sensor arrays that can sense load, relative humidity and temperature with high resolution and short response times. Artificial and/or electronic skin may be integrated in medical prosthesis and robotics industries. Additional applications include, but are not limited to, use by individuals in order to keep track of loads they carry (e.g. harbor employees) and measure their physical response including body temperature and humidity; and use to cover engines of cars and planes which can be configured to set alarms once excess temperature or pressure are being detected and/or early formation of cracks initiates.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth. It should be noted that the term "and" or the term "or" is generally employed in its sense including "and/or" unless the content clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Synthesis of MCNPs:

Gold (III) chloride trihydrate ($HAuCl_4 \cdot 3H_2O$), tetraoctylammonium bromide (TOAB), sodium borohydride, 3-ethoxythiophenol (ETP), decanethiol (DT) and 2-nitro-4-trifluoro-methylbenzenethiol (NTMBT) were purchased from Sigma-Aldrich. All reagents were of analytical grade and were used as received. Spherical gold nanoparticles (AuNPs; 3-6 nm in diameter) were synthesized as described in Peng et al., Nature Nanotech. 2009, 4, 669-673; and Dovgolevsky et al., J. Phys. Chem. C. 2010, 114, 14042-14049; the content of each of which is hereby incorporated in its entirety. Briefly, a solution of $HAuCl_4$ was added to a stirred solution of TOAB in toluene. After 10 min stirring, the lower aqueous phase was removed. Organic ligands and sodium borohydride were subsequently added to the toluene phase. After 3 hours at ice temperature, the lower aqueous phase was removed and the toluene phase was subsequently evaporated by rotary evaporation. After first washing with cold ethanol, the solution was kept at 5° C. for 18 hours until complete immersion was achieved. The dark brown precipitate was filtered off and washed with ethanol.

Sensor Fabrication:

Electrodes were deposited on different isolating substrates (Table 1). The electrodes were prepared using silver paste (Mouser Electronics). The spacing between the electrodes was typically 1 mm in all experiments that examined the substrate effect on the load sensitivity. Similar printed electrodes with variable spacing of 0.5, 1 and 3 mm were used in order to examine the effect of spacing between the electrodes. Stretching was performed on "dog bone" samples cut from the same substrate as in the bending experiments. Electrodes were prepared in a similar manner using silver paste with 1 mm spacing between the electrodes. The substrates were obtained from DuPont (GADOT as distributers). Flexible sensors were prepared by casting 2 μl of MCNPs in solution on top of the flexible substrates/electrodes.

Morphology Characterization of the MCNP Layers:

The microstructure and morphology of the MCNP films were characterized by field emission high-resolution scanning electron microscopy (Carl Zeiss Ultra Plus FE-HRSEM). The FE-HRSEM analysis was performed using two main detectors: secondary electrons (SE) detector and back scattered electrons (BSE) detector. The SE detector provides high-resolution imaging of the surface. The BSE detector provides image contrast as a function of elemental composition as well as surface topography.

The morphology of the MCNP films was additionally examined by a tapping mode atomic force microscope (AFM) (Dimension 3100 with Nanoscope Ma controller, Veeco Instruments Inc.) that is equipped with a 100×100 μm$^2$ scanner. Silicon cantilevers with a normal resonance frequency of 160 kHz and spring constants of 5 N/m (NSCL$_4$/AlBs, MikroMasch, Estonia) were used. All images were captured with a scan rate of 1-2 Hz and a pixel resolution of 512×512.

The Set-Up of Bending Experiments:

A MARK 10 ESM301 motorized test stand was used to apply a constant strain of 1.5 mm/sec. For bending setup (FIG. 22A), the stress was applied by an upper beam which is indicated by the upper arrow, and the lower beams were used as supporting beams. Under applied stress/pressure/force, the substrate was bent. The outer (upper) surface was then subjected to compression, while the inner (lower) surface was subjected to dilatation. The forces were measured by Advanced Digital FORCE GAUGE, made by Mark10 USA.

The Set-Up of Stretching Experiments:

Strain/force was applied between 2 metal grips on a "dog bone" sample that is illustrated in FIG. 22B. The arrows represent the direction of stretching. A MARK 10 ESM301 motorized test stand was used to apply a constant strain of 1.5 mm/sec between metal grips that were attached to the wider part of the sample, while most of the strain occurred in the thinner part of the sample. The forces were measured by Advanced Digital FORCE GAUGE, made by Mark10 USA.

Figure 17:
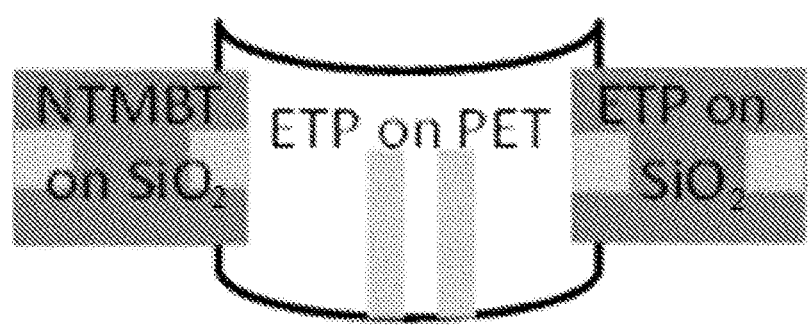
FIG. 17: A schematic illustration of a prototype platform for sensing humidity, RH and load using different substrates (PET substrate at the center and silicon dioxide substrates at the sides) and 2 different MCNPs (ETP at the center and NTMBT at the sides). The lines crossing the substrates represent metal electrodes.

Preparation of the Integrated Pressure/Temperature/Humidity Sensors:

Humidity or temperature sensors based on MCNP layers on $SiO_2$ substrate were prepared by drop casting aliquots of MCNP solution on interdigitated electrodes consisting of 24 pairs of Au electrodes (5 μm width and 25 μm spacing between adjacent electrodes) on a silicon wafer with a 1000 nm $SiO_2$ film. Between those sensors, a flexible ETP-MCNP layer on PET substrate was placed (FIG. 17). The electrodes on the PET were mash printed by CPC Hi Technologies Ltd. with spacing of 1 mm.

The Set-Up of Evaluation of Temperature and Relative Humidity Sensing Experiments:

Twenty sensors were mounted on a custom PTFE circuit board. The board was mounted into a stainless steel test chamber with a volume of less than 300 cm$^3$. For controlling the relative humidity levels (5-60% RH), purified dry nitrogen (99.9999%) from a commercial nitrogen generator (N-30, On Site Gas Systems, USA) equipped with a nitrogen purifier was used as a carrier gas. The dry nitrogen was mixed with humidified air generated by the system's humidifier module. Controlled temperatures were produced by a custom-made temperature controller. The sensing experiments were performed by monitoring the response of the MCNP and environmental sensors (RH, temperature) to different relative humidity and temperature levels generated by the system.

During ambient sensing experiments (Tables 3-4 and FIG. 20), monitoring of the response of the MCNP and environmental sensors (RH, temperature and force gauge sensors) to different relative humidity and temperature levels in a room while using an applied force on the tested sensor was performed. A Keithleydatalogger device (model 2701 DMM) controlled by a custom Labview program was used to sequentially acquire resistance readings from the sensor array and voltage readings from the environmental sensors.

Figure 24:
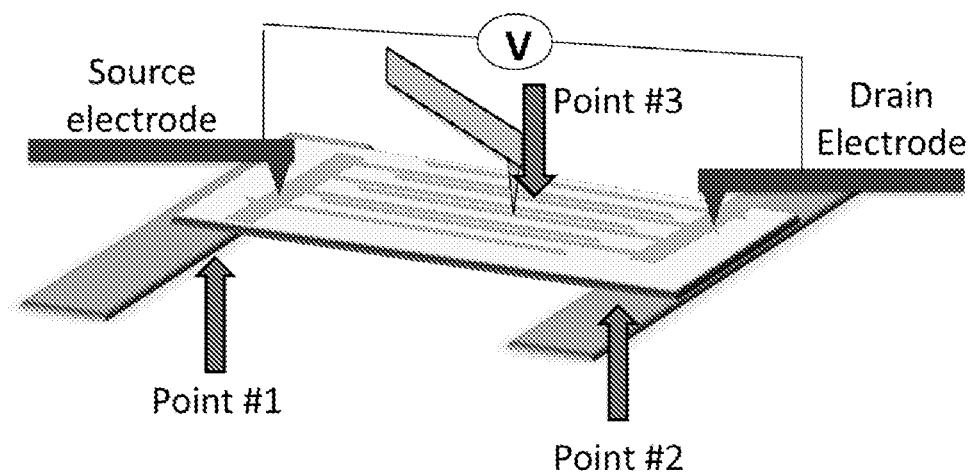
FIG. 24: A schematic illustration of the three-point bending setup. Point #1 and point #2 are the static lean beams on which the flexible substrate rests. Point #3 is where the pressure is applied, using a disconnected, screw-controlled probe. The resistance of the MCNP film is measured through the drain and source electrodes.

MCNP-Based Pressure Sensor:

The sensors were prepared on polyethylene (PE) substrates. Ten pairs of 4.5 mm wide, interdigitated (ID) electrodes with an inter-electrode spacing of 100 μm were formed on the substrates by evaporation of 20 nm/200 nm Ti/Au layer through a shadow mask. Chemiresistors were prepared by drop casting aliquots of representative MCNP solutions. A homemade three-point bending system was used in a probe station. Under applied force, the beam that is subjected to the three-point bending test is bent downwards as schematically illustrated in FIG. 24. The outer (upper) surface is then subjected to compression, while the inner (lower) surface is under strain. The stress (or compression) can be calculated from the measured deflection of the sample, according to the equations below:

The moment of inertia (I) for a rectangular sample (FIG. 23):

$$I = \frac{b \cdot h^3}{12} = 1.3 \cdot 10^{-3} \text{ mm}^4$$

The surface area (A):

A=20 mm$^2$

The applied pressure (P):

$$P = \frac{48EI\delta}{L^3}$$

Where E is the Young's modulus and δ is the deflection of the center of the sample. For example, when using polyethylene as a substrate, $\delta_{minimum}$=0.075 mm, the Young's modulus is 500 MPa, and the pressure for each deflection value:

$$P = 0.032 \cdot \delta$$

Using the minimal measured deflection value of 0.075 mm, the sensor was subjected to a load of 0.24 gr:

$$P(\delta=0.075 \text{ mm}) = 2.4 \cdot 10^{-3} N = 0.24 \text{ gr}$$

and the resulting calculated stress (σ) is:

$$\sigma = \frac{P}{A} = 1.2 \cdot 10^{-4} \text{ MPa} = 0.12 \text{ KPa}$$

The probe station, connected to a device analyzer (Agilent B1500A), was used to collect the electrical signals of the MCNP-based pressure sensor during bending and stretching. Resistance as a function of time was measured under constant voltage of 0.5V.

Example 1

Sensing Temperatures and Humidity

The possibility to integrate temperature and humidity sensing capabilities within the MCNP-based touch platforms was examined. For this purpose, nitro-4-trifluoromethylbenzenethiol (NTMBT) MCNP sensors were placed in a vacuum chamber with a controllable environment. The temperature or relative humidity (RH) was altered in a stepwise manner, and the corresponding $\Delta R/R_b$ was monitored. FIG. 1A presents the $\Delta R/R_b$ of the sensor upon elevation of the temperature. $\Delta R/R_b$ was linear and decreased by 1% with each 1.33° C. increase in the temperature, making this sensor sensitive enough to monitor the fluctuations of the temperature in the surrounding environment. A zoom into the temperature regime of 35-39° C. shows that the sensitivity of the NTMBT-MCNP-based sensor is high enough to act as a human body thermometer able to precisely detect fluctuations as small as 1° C. or the presence of a heat source in the vicinity of the artificial or electronic skin, without the need for touching the object. The ability of the sensors to sense temperature was further demonstrated using NPs films deposited on several slides, including Kapton® 200 μm thick and a PVC slide having a much larger thickness. All devices exhibited a very strong response to ambient temperature changes: baseline resistance shifts of 1% as a response to 1° C. change in temperature. Next, 4 devices were manufactured on the same Kapton® slide, and connected to a resistance-measurement device. All four resistance values were repeatedly measured with a cycle time of ~1 sec. The devices were placed face down on a non-flexible platform. Once a hot object (human hand) was brought to the proximity of each (or all) sensor, the baseline resistance changed towards lower values. This phenomenon was repeated whenever the hot object was close (1-5 cm) to the device. This effect was reversible upon removal of the hot object and was not observed when the object was at the same temperature as the sensor. The response times of the sensors were approximated at about 1 sec, namely a significant shift in the baseline resistance approximately 1 second after a human hand was placed in the proximity of the sensors was observed. Within 15 seconds, the resistance had changed by ~4-6% for all 4 sensors. Thus, the sensors and platform unit of the present invention are very sensitive to temperature and heat and can sense a hot object brought to their vicinity in a short period of time. The temperature difference between the devices' temperature and the human hand brought to its vicinity was ~15° C.

Figure 1B:
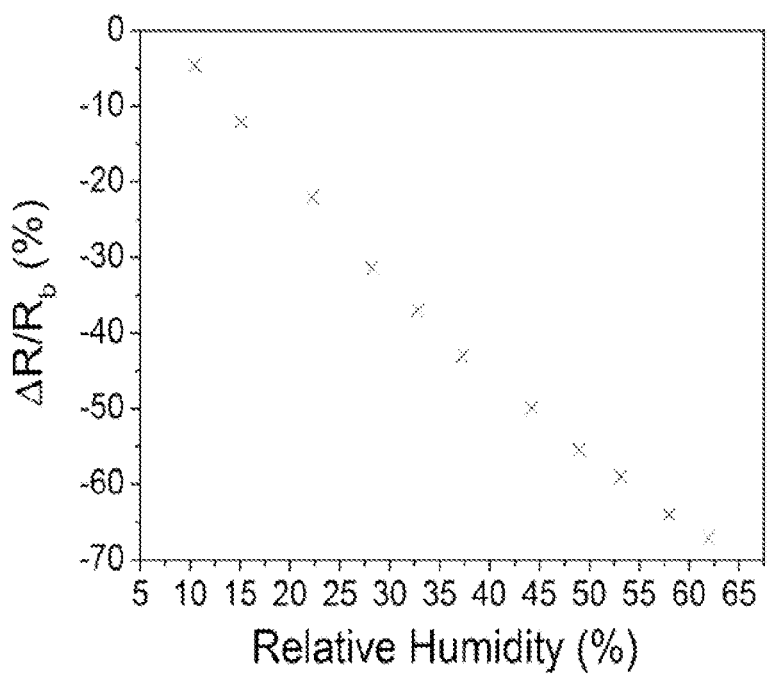
Figure 2:
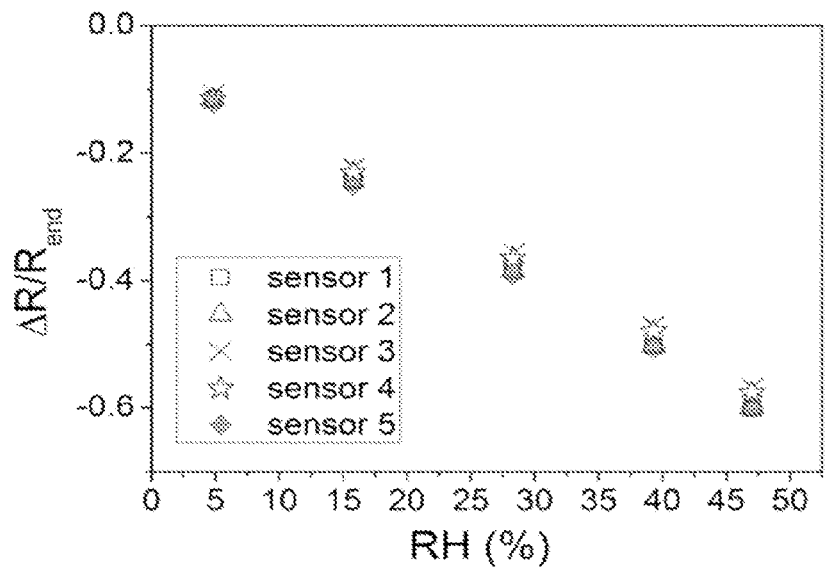
FIG. 2: Relative responses of five duplicated MCNP-based sensors to increase in relative humidity levels.

FIG. 1B shows the relative responses of a NTMBT MCNP-based sensor in a humidity region that exists in most environmental applications (5-60% RH). The magnitude of the relative response is linearly proportional to the measured RH levels, with a sensitivity that is down to a single percent RH. Duplicated sensors exhibited good agreement in response to different levels of RH (FIG. 2). Specifically, 5 duplicates of the humidity sensors were tested to evaluate the reproducibility of production and performance. All 5 duplicated MCNP-based sensors exhibited essentially the same response magnitudes to all tested RH levels, with a linear dependence on the RH level. These results emphasize the possibility of producing and integrating temperature and humidity sensors as part of an artificial or electronic skin application based on sensors of NTMBT MCNPs.

Example 2

The Effect of Stretching and Bending on the Flexible MCNP Sensors

Figure 3A:
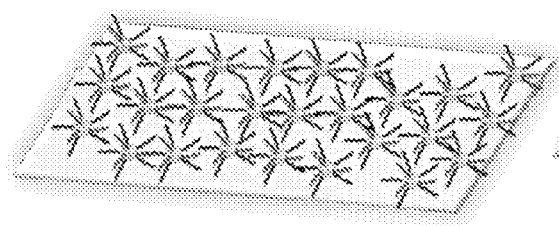
FIGS. 3A-3I.
Figure 3B:
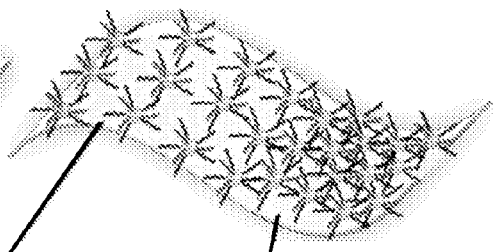
Figure 3C:
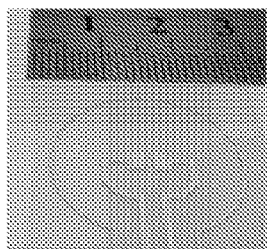
Figure 3D:
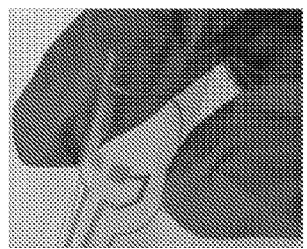
Figure 3E:
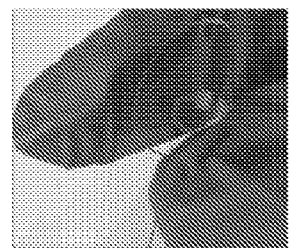
Figure 3F:
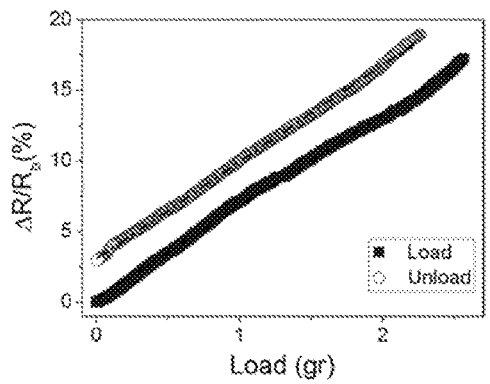
Figure 3G:
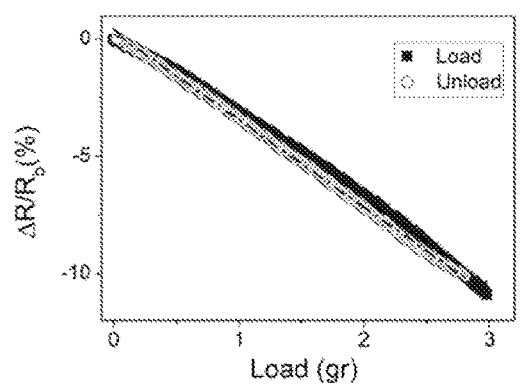
Figure 3H:
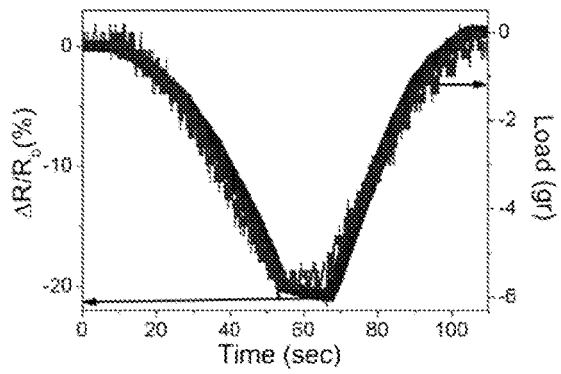
Figure 3I:
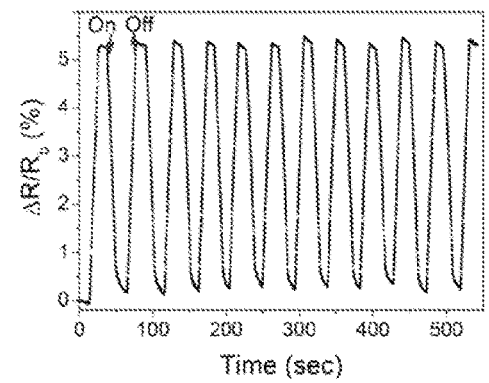

Pressure sensors of gold nanoparticles capped with 3-ethoxythiophenol ligands (ETP-MCNP) on flexible polyethylene terephthalate (PET) substrates were examined by a three-point bending test, under bending and stretching conditions. All experiments were performed at the room temperatures of 20° C.±1° C. and relative humidity (RH) levels of 50%±3%. FIGS. 3F-3G present load and unload curves of the ETP-MCNPs strain sensor on PET substrate. The relative resistance responses ($\Delta R/R_b$, where $R_b$ is the baseline resistance with no load applied on the sensor, and $\Delta R$ is the change in resistance between $R_b$ and the resistance with load is applied on the sensor) were obtained when the ETP-MCNP films were stretched in one case and compressed in the other case. The positive or negative changes in resistance were linear upon gradual change of the bending level of the PET substrate. When the ETP-MCNP film was placed on the top side of the PET substrate, bending the substrate resulted in a compression of the ETP-MCNP film thereby bringing the ETP-MCGNPs closer to each other and allowing higher tunneling currents. Accordingly, a decrease in measured resistance was obtained (FIGS. 3E and 3G). When the ETP-GNPs film was placed on the bottom side of the PET substrate, bending the substrate increased the distance between the adjacent ETP-GNPs, resulting in a smaller tunneling current and, therefore, an increase in measured resistance (FIGS. 3D and 3F). FIG. 3H shows the ETP-MCNP sensor responses upon continuous compression with time. Load and unload are represented by a thick line and load change is represented by a thin line. The sensors response closely follows the load curve. The maximum load is about 6 gr and the corresponding response is ~20%. In addition, the baseline resistance of the sensor after the load-unload cycle is similar. FIG. 3I shows the high repeatability of the response of the ETP-MCNP sensor to stretching when subjected to 12 cycles of load (0.75 gr) and unload. As seen in the figure, the change in the relative resistance response to the load is about 5%. The sensor's response is repeatable with 1.5% relative standard deviation of the response (5%±0.075%) and ~2% relative standard deviation of baseline resistance values. The load units are presented in grams wherein a load of 1gr is comparable to approximately 0.01N.

Figure 4A:
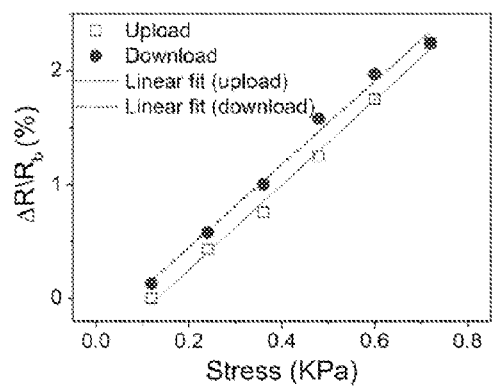
FIGS. 4A-4D: $\Delta R/R_b$ of DT-GNP-based sensor to (FIG. 4A) stretching and (FIG. 4B) compressing the PE substrate by uploading (□) and downloading (■) of stress during three-point bending experiment. The responses are linear and repeatable.
Figure 4B:
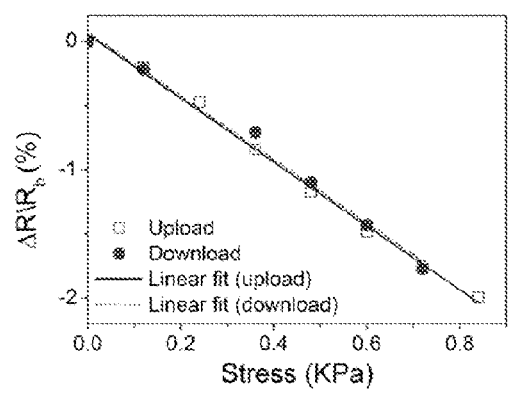
Figure 4C:
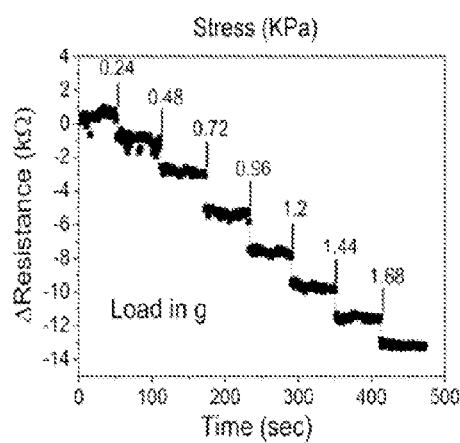
Figure 4D:
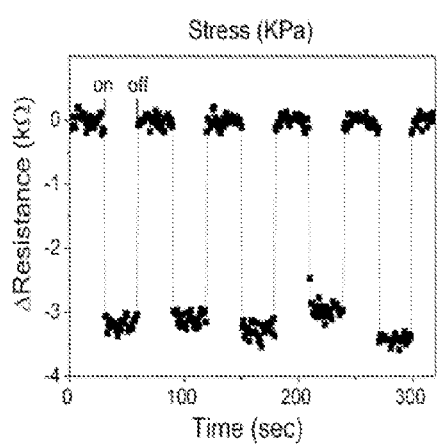

Similar results were obtained using gold nanoparticles capped with decanethiol (DT-MCNP) on flexible polyethylene (PE) substrate. The DT-MCNP film was subjected to bending and stretching. FIGS. 4A-4B present load and unload curves of the DT-MCNPs strain sensor on polyethylene (PE) substrate, subjected to a three-point bending test. The relative resistance sensing signals ($\Delta R/R_b$) show linear positive or negative changes in resistance upon gradual decrease or increase of the bending level of the PE substrate. When the DT-MCNP film was placed on the PE's top side, bending the substrate compressed the DT-MCNP film thus decreasing the distance between adjacent DT-MCNPs, thereby allowing higher tunneling currents and a decrease in measured resistance (FIG. 4B). When the DT-MCNP film was placed on the PE's bottom side, bending the substrate increased the distance between adjacent DT-MCNPs, resulting in a smaller tunneling current and, therefore, increased measured resistance (FIG. 4A). There is a significant hysteresis between the load and the unload curves in FIG. 4A. The sensitivity limit is down to tens of Pa, with 20 Pa being the limit of detection for this specific substrate. In the current setup, 20 Pa equals to ~400 mg placed on an area of 20 mm$^2$. As seen in FIG. 4C, by applying loading steps of about 0.24 gr, a change in resistance of more than 1 KΩ was obtained. The noise was reduced as the weight loaded on the sensor increased. However, weight loads as low as a quarter of a gram were easily detected above the noise level. Stretching of the same sensor resulted in similar load inset, but with positive shifts in the resistance. FIG. 4D shows the repeatability of the response when cycles of load and unload of repeated stress of 250 Pa on the DT-MCNP sensor were performed. The calculated signal-to-noise ratio of the response was about 38, with response times less than 1 second.

To estimate the range of load sensitivities, similar measurements were performed on several substrates with different elastic properties. Three-point bending calculations were performed on several substrates with different elastic properties (different Young modulus) as follows: PDMS (Young's modulus of 360-870 KPa; PE (Young's modulus of ~500 MPa); SiO$_2$ (glass; Young's modulus of ~70 GPa); and Si rubber (Young's modulus of ~75 KPa). For minimal load estimation, using the lowest measured deflection value of 0.075 mm, the sensor was subjected to a load of 0.24 gr on a PE substrate. To achieve the same level of deflection (the deflection is proportional to the strain and the change of resistance) when using PDMS as a substrate under the same experimental conditions, the sensor would have to be subjected to a load of only 0.24 mg and thus a lower detection limit would be achieved. When using glass as the substrate, measuring of higher values of stress compared to a PE substrate while maintaining similar strain levels can be obtained. Hence, using a deflection value of 0.525 mm, a DT-MCNP-SiO$_2$ platform would need to be subjected to a load of 238 gr to achieve similar deflection to that achieved when the DT-MCNP-PE platform was subjected to a load of 1.7 gr.

When using PDMS as a substrate, the sensor was sensitive to a load of 0.24 mg. DT-MCNP on glass (SiO$_2$) provided sensitivities of higher loads (238 gr) than the sensitivities obtained for DT-MCNP on PE (1.7 gr). When Si rubber was used as the substrate (DT-MCNP—Si rubber platform), the calculated limit of detection was lower by eight-fold in comparison to the DT-MCNP-PE platform.

A tunable load sensor based on ETP-MCNP layer casted on a flexible substrate is presented. The low standard deviations and the high signal-to-noise ratios of the signal's output for repeated load in FIG. 3I, assure repeatable measurements of the sensors. When bending increases the distance between the nanoparticles, there is an offset between the load and unload sensing curves. Without being bound by any theory or mechanism of action, this offset can be attributed to irreversible changes in the ETP-MCNP layer (e.g. the formation of cracks; Olichwer et al., ACS Appl. Mater. Interf. 2012, 4, 6151-6161) or MCNP displacement.

Example 3

The Effect of the Substrate on the MCNP Layer Morphology and on the Related Sensing Properties The relative response of the sensors is directly proportional to the deflection (for a certain bending set-up). Accordingly, when introducing larger deflections, the responses of the flexible sensors increase. Since large deflections can cause irreversible changes both to the flexible substrate as well as to the MCNP layer, a range of load sensitivities is required. In this manner, high loads are measurable using thick substrates having high Young's modulus and small loads are measurable using thin substrates having low Young's modulus.

The relation between the properties of the substrate and the MCNP-based load sensors was explored by deposition of ETP-MCNP films on: (i) substrates having similar composition (e.g., the same polymer) but different thicknesses; and (ii) substrates having different compositions (e.g., different polymers) but similar thicknesses (e.g., 50 μm thick substrates). The flexible substrates and their properties are listed in Table 1.

TABLE 1

Fabricated MCNP/substrate sensors

| Substrate | Young's modulus (MPa) | Substrate thickness (μm) | Load Sensitivity[a] |
|---|---|---|---|
| PVC 200 | 2200 | 200 | 0.04 ± 0.003 |
| Kapton ® 50 | 2500 | 50 | 0.23 ± 0.03 |
| Kapton ® 127 | 2500 | 127 | 0.04 ± 0.014 |
| Kapton ® b. 131 | 4430 | 131 | 0.03 ± 0.008 |
| PET 125 | 4200 | 125 | 0.01 ± 0.005 |
| Mylar ® 36 | 4100 | 36 | 0.31 ± 0.036 |
| Mylar ® 50 | 4100 | 50 | 0.07 ± 0.019 |

[a]load sensitivity: relative change of resistance per unit change in the load.

The surface morphology of ETP-MCNP films on different substrates was studied by field emission high-resolution scanning electron microscopy (FE-HRSEM) and atomic force microscopy (AFM). FIGS. 5A-5C show the surface morphology of ETP-MCNP film on Mylar® 36. FIG. 5A shows the film's margins at low magnification (×200). The layers were deposited by drop-casting the GNP solution onto the substrates. Cracked "coffee ring"-like surface structures, several hundreds of microns in diameter, which were formed during the deposition process are seen. At the center of the drop (left side of FIG. 5A and FIGS. 5B-5C) a continuous film was formed. The layer thickness varied between 400 and 900 nm at the center of the drop (as estimated by AFM measurements). A higher magnification (×30,000) of the center revealed small "bubble-like" structures, part of which having cracked centers (FIGS. 5B-5C). Examining those cracks with back scattered electrons (BSE) analysis (FIG. 5C) showed darker color as compared to other regions on the ETP-MCNP film, implying that the cracks which are tens of nanometers deep, expose the layer-substrate-interface. FIGS. 6A-6G show the ETP-GNP layer margins (which are characterized by the drop "coffee ring"-like surface structures) of (FIG. 6A) Kapton® 50, (FIG. 6B) Kapton® 127, (FIG. 6C) PET 125, (FIG. 6D) Kapton® b. 131, (FIG. 6E) Mylar® 36, (FIG. 6F) Mylar® 50 and (FIG. 6G) PVC 200. The high magnification (×30,000) of these figures reveals deep cracks that reach the polymer substrates. These cracks result in non-conductance of the layer margins. Images taken at lower magnification show that this phenomenon is widespread and occurs for a variety of substrates (FIGS. 7A-7G).

FIGS. 8A-8G show the center of a deposited drop of ETP-MCNP on various substrates. Similar surface morphology of the ETP-MCNP layers on the different substrates exists. Excluding PVC 200, all substrates exhibited highly continuous films, with different substrates resulting in different density of the "bubble-like" structures. For PVC 200, cracks appeared over the entire layer. Nevertheless, continuous surface areas were observed (FIG. 8G). Without being bound by any theory or mechanism of action, the morphology of the "coffee ring" and "bubbles" in the inner part of the layer can be explained by the capillary flow in drops upon drying (Deegan et al., Nature 1997, 389, 827-828; Deegan et al., Phys. Rev. E 2000, 62, 756-765; and Deegan, Phys. Rev. E 2000, 6, 475-485). The difference in the "bubble" density might be attributed to the different adhesion between the ETP-MCNP solutions and the different substrates, which, in turn leads to different capillary forces during the drying process of the drop. The similar morphology obtained for most substrates used assures that the comparison between ETP-MCNP layers on different substrates is mainly affected by the substrate and not by the morphology differences of the ETP-MCNP layer.

Figure 9A:
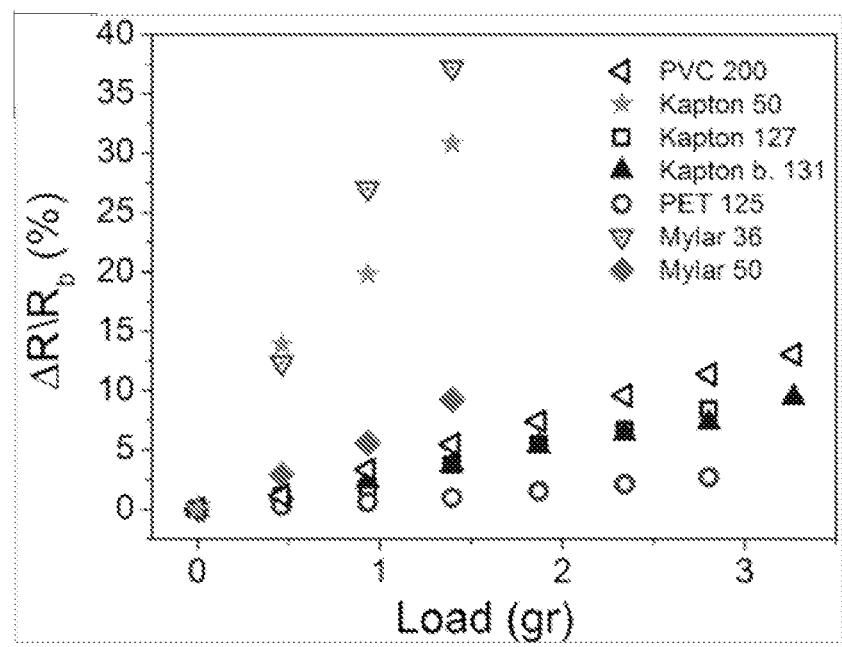
FIGS. 9A-9B.
Figure 9B:
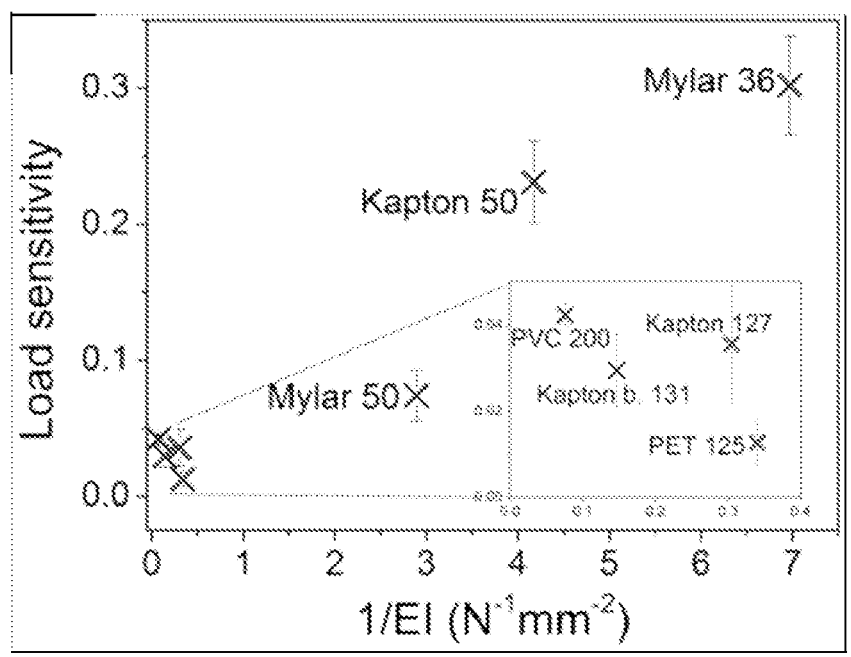

FIG. 9A shows the response of the pressure sensors as measured by three-point bending tests. All experiments were performed while maintaining room temperature at 20° C.±1° C. and relative humidity level at 50%±3%. The electrical measurements were performed using silver electrodes with 1 mm spacing between the electrodes. The sensors were tested under a series of loads (0.5-3.5 gr) and the average responses ($\Delta R/R_b$) were calculated from 3-5 duplicates. The response increased linearly with increasing the load (FIG. 9A). FIG. 9B shows the load sensitivity of the sensors having substrates with different properties, as a function of the Young's modulus, geometrical property, and moment of inertia. The slope indicates that the load sensitivity depends on the substrates' mechanical and geometrical properties. Applying a specific load on different substrates that are coated with similar ETP-MCNP layers exhibited noticeable differences in the response. For example, applying a load that is equal to 0.9 gr on Kapton® b. 131 coated with a ETP-MCNP film, yielded a lower response (~3%) than the response obtained using Mylar® 36 as a substrate that is coated with a similar ETP-MCNP film (~27%). This difference could be attributed to the larger elasticity of the Mylar® 36 substrate. Without being bound by any theory or mechanism of action, the larger elasticity of the Mylar® 36 substrate may lead to a larger separation between the ETP-MCNPs of the sensing layer (when the ETP-MCNPs film is at the bottom side of the substrate; Alvares et al., Procedia Eng. 2011, 25, 1349-1352). The slope of the relative resistance versus the load provides the sensor's load sensitivity, which depends on the Young's modulus, E, and on the moment of inertia, I as follows:

$$I = \frac{bh^3}{12}$$

where b is the substrate's width (which was substantially similar in all substrates used) and h is the substrate's thickness. The relation between the sensor's sensitivity, load, and the substrate parameters is provided by the following equation:

$$\frac{\frac{\Delta R}{R_b}}{\Delta P} \propto \frac{1}{EI}$$

where $\Delta P$ is the load change. FIG. 9B shows the average load sensitivities of the substrates as a function of their Young's modulus and the moment of inertia. The load sensitivity clearly depends on the substrate properties. Specifically, there is a correlation between the thickness of the substrate and its Young's modulus and the load sensitivity where thinner substrates having lower Young's modulus possess higher load sensitivity. The error bars in FIG. 9B represent the standard deviation of 3-5 similar substrates. For most substrates, the standard deviation is one order of magnitude smaller than the load sensitivity mean value.

Figure 10A:
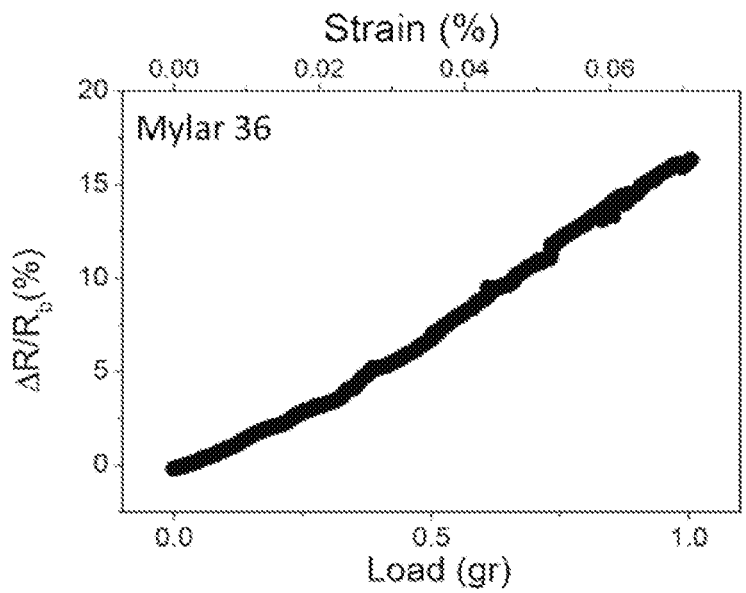
Figure 10B:
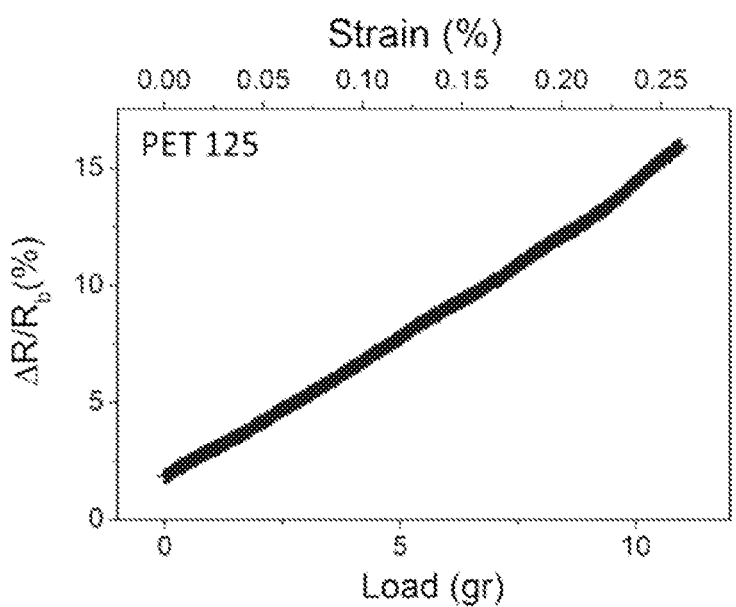

To estimate the range of the load sensitivities, two types of sensors were examined under various loads: (i) an ETP-MCNP film deposited on Mylar® 36 (load sensitivity=0.31) subjected to 200 mg-1 gr loads; and (ii) an ETP-MCNP film deposited on PET 125 (load sensitivity=0.01) subjected to 200 mg-10 gr loads. FIGS. 10A-10B show the $\Delta R/R_b$ versus the load (bottom x-axis) and the strain (upper x-axis). By changing the substrate's type, a change in the sensor's response to a specific load and strain is obtained. When a high response to low strains and loads is required, a sensor having high load sensitivity, e.g. Mylar® 36 that has ~15% response to 1 gr load and 0.07% strain (FIG. 10A), can be used. When higher strains and load range are applied, a sensor having smaller load sensitivity, e.g. PET 125 that can sense up to 10 gr load and 0.25% strain (FIG. 10B), can be used.

Figure 11A:
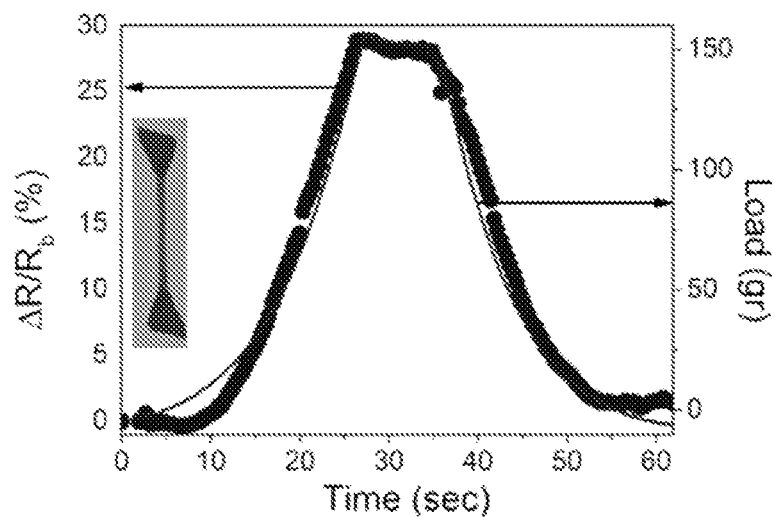
FIGS. 11A-11B.
Figure 11B:
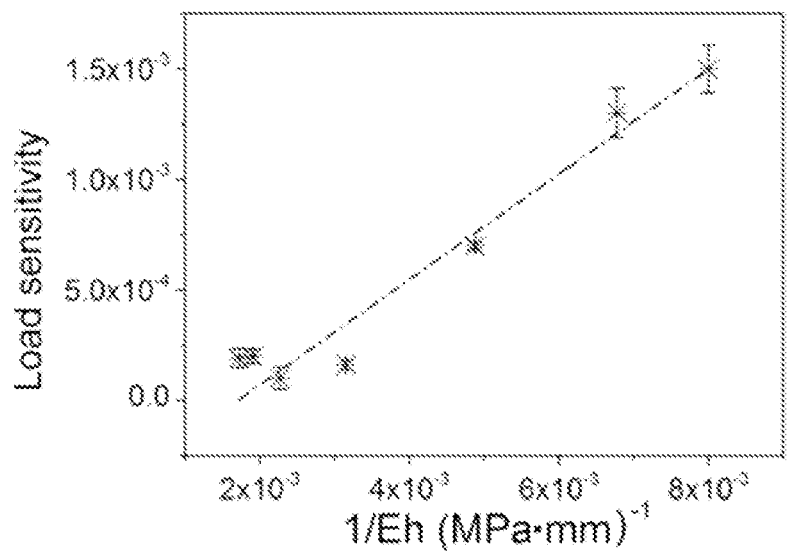

Stretching properties of the ETP-MCNP-based sensors were tested. "Dog bone" samples (FIG. 11A; inset) were prepared and stretched in "Mark 10" motorized test stand while measuring the force in a complementary force gauge. Stretching a sample, while applying forces in the substrate's linear elastic regime of the stress-strain curve, follows the Hocks law:

$$\sigma = \in E$$

where σ is the applied force divided by the cross sectional area, ∈ is the strain in the sample and E is the Young's modulus. In this setup, the width of all of the sensors was substantially equal. Therefore, the load sensitivity is expressed by:

$$\frac{\frac{\Delta R}{R_b}}{\Delta P} \propto \frac{1}{Eh}$$

where h is the substrate thickness. FIG. 11A shows the ETP-MCNP sensor response (thick line) upon continuous stretching load and unload (thin line) with time. The sensor's response closely followed the load curve. The maximum load was about 150 gr with a ~27% corresponding response. The baseline resistance of the sensor after the load-unload cycle was similar. FIG. 11B presents the load sensitivity as a function of the substrate's Young's modulus and thickness. The error bars are the standard deviation of 3 similar sensors. There load sensitivity clearly depends on the properties of the substrate. For stretching, the applied forces are significantly larger and the load sensitivities are smaller.

Hence, there is a direct link between the substrate's properties and the measured load sensitivities, both in bending setup (FIGS. 9A-9B) and in stretching setup (FIGS. 11A-11B). The non-linearity can be attributed to different adhesion between the ETP-MCNP film and the various substrates. It is, however, evident that the load sensitivity can be modulated by controlling the properties of the substrate, using the same MCNP ligands. This obviates the need for extensive and expensive synthesis procedures for producing different MCNPs to achieve a desired sensing functionality.

Example 4

Fine Tuning of the Sensing Properties of the Flexible MCNP Sensors

Figure 12A:
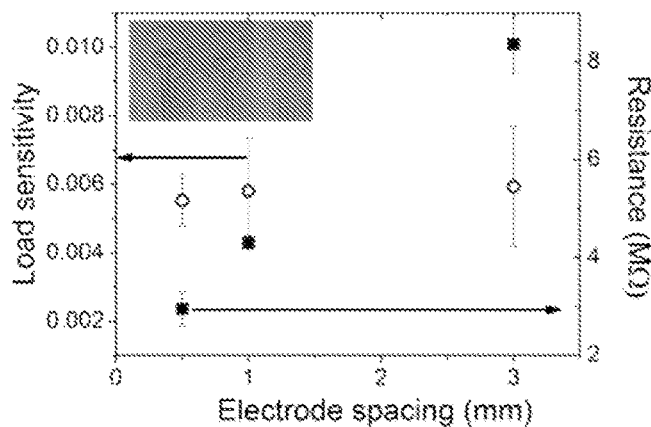
FIGS. 12A-12C.

For determining the factors which control the load sensitivity of the sensors, additional parameters were examined as follows: (i) electrode spacing; (ii) substrate related parameters (e.g. width); and (iii) MCNP film related parameters (e.g. capping ligand). In order to determine the electrodes' spacing effect, ETP-MCNP layer was casted on electrode spacing ranging from 0.5-3 mm. The error bars are the standard deviation of 3 tested sensors for specific electrode spacing. FIG. 12A shows that the spacing between the electrodes has a negligible effect on the load sensitivity. In contrast, the spacing between the electrodes dramatically changed the baseline resistance. For example, ETP-MCNP film casted on electrodes spacing of 1 mm showed a typical baseline resistance of 4MΩ, while a similar ETP-MCNP film casted on 3 mm electrodes spacing showed a baseline resistance of 8MΩ (FIG. 12A). Without being bound by any theory or mechanism of action, it is contemplated that the load sensitivity is independent on the baseline resistance. Images of the electrodes structure are presented in the inset of FIG. 12A.

Figure 12B:
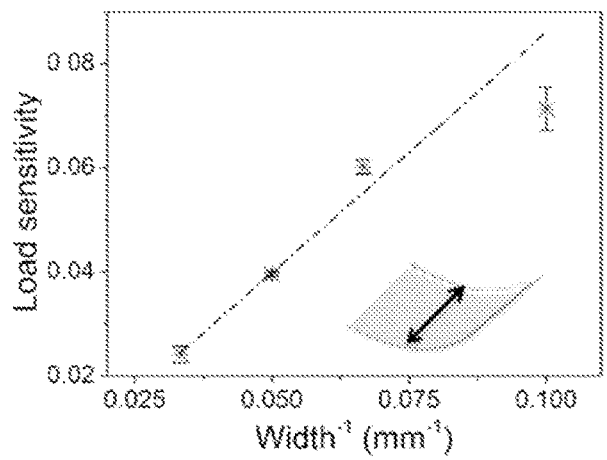

FIG. 12B demonstrates that it is possible to control the load sensitivity, using ETP-MCNP layer casted on Kapton® 127 having different substrate dimensions. The error bars in the figure are the standard deviation of 3 repetitions of the same sensor that is located on a substrate having specific dimensions. By cutting the substrate width from 30 mm to 10 mm, the load sensitivity was improved by a factor of 3.5.

Figure 12C:
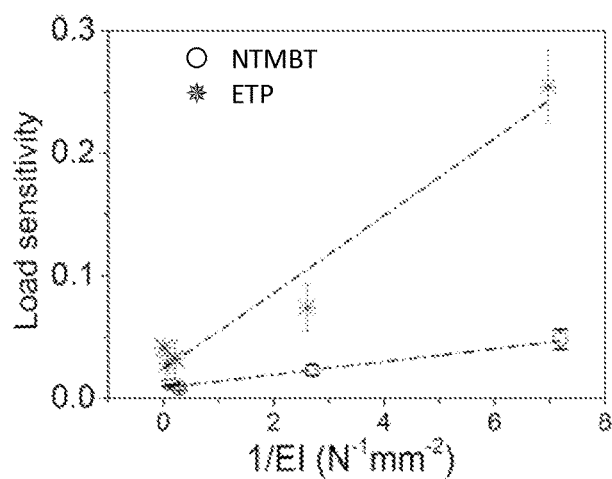

An additional factor which controls the sensitivity of MCNP-based flexible sensors is provided by changing the capping MCNP layer. The MCNPs' organic ligands determine the chemical bonds' type and strength between neighboring MCNPs thereby affecting the load sensitivity. The tunneling decay constant which determines the change in resistance is also affected by the capping ligands. FIG. 12C presents the change in load sensitivity when replacing the capping ligand from ETP to nitro-4-trifluoro-methylbenzenethiol (NTMBT) and casting both MCNPS on 5 different substrates (represented in the x-axis by their Young's modulus, E, and by their moment of inertia, I). The error bars are the standard deviation of 3 similar sensors. There is a positive correlation between the load sensitivity and the properties of the substrate for both ETP-MCNP and NTMBT-MCNP films. Nevertheless, all NTMBT-MCNP sensors exhibited lower load sensitivities.

Hence, by adjusting the substrate width and/or changing the capping ligand in the MCNP sensor, a control over the load sensitivities can be obtained.

Example 5

Flexible MCNP Sensors as Strain Gauges

Figure 13:
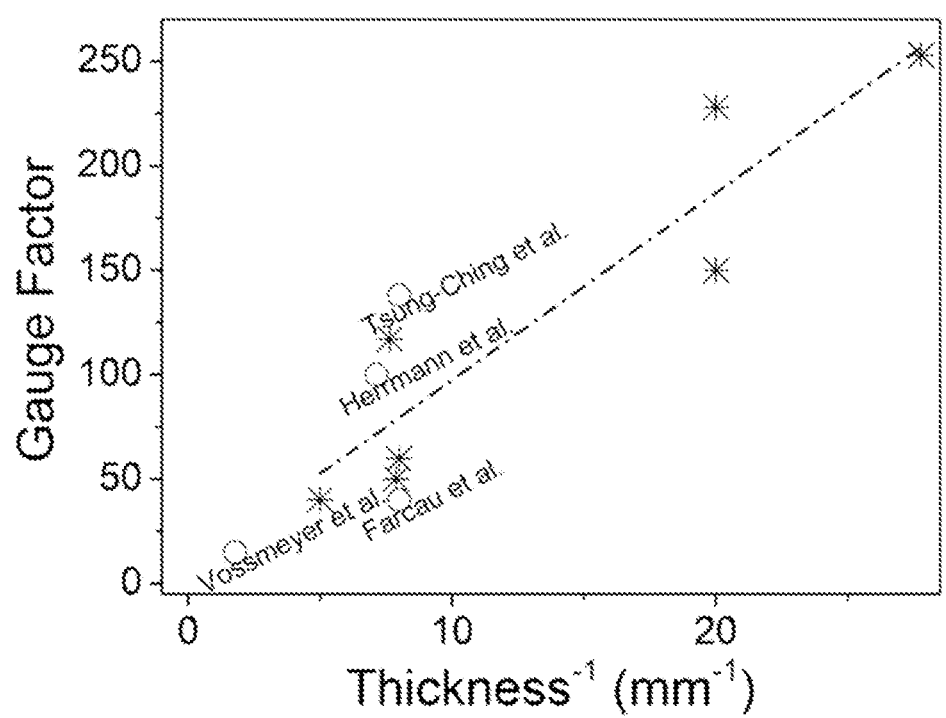
FIG. 13: Gauge Factor (GF) values that were extracted from linear fits of the sensors' relative response vs. the strain. The asterisks represent the results described herein and the circles are GF values from Farcau et al., ACS Nano 2011, 5, 7137-7143; Tsung-Ching et al., J. Disp. Tech. 2009, 5, 206-215; Vossmeyer et al., Adv. Funct. Mater. 2008, 18, 1611-1616; and Herrmann et al., Appl. Phys. Lett. 2007, 91, 183105. The dashed line represents a linear fit.

FIG. 13 shows the Gauge Factor (GF) of ETP-MCNP sensors (asterisks). GF measurement characterizes the sensitivity of the sensors as strain gauge, viz. the ratio between $\Delta R/R_b$ and $\in$. The GF is the slope of linear fit of the sensors' relative response curves as a function of the strain. In the bending setup, the strain is proportional to the substrate thickness and the GF is inversely proportional to the thickness of the substrate. FIG. 13 shows an inverse linear correlation between the GF and the thickness of the substrate. A GF of 250 could be achieved with ETP-MCNP films deposited on thin substrates (36 μm). This GF value is at least two times higher than previously reported nanoparticle-based strain gauges presented by hollow circles in FIG. 13 and Table 2.

TABLE 2

Gauge sensors

| Nanoparticle diameter (nm) | GF | Substrate |
|---|---|---|
| 14 | 35-41 | PET[a] 125 μm[c] |
| 18 | 135 | PET[a] 125 μm[d] |
| 4 | 10-20 | LDPE[b] 560 μm[e] |
| 18 | 100 | photoresist 140 μm[f] |
| 2-5 | 50-250 (substrate depended) | Variety of substrates |

[a] PET = Polyethylene terephthalate
[b] LDPE = Low-density polyethylene
[c] Farcau et al., ACS Nano 2011, 5, 7137-7143
[d] Tsung-Ching et al, J. Disp. Tech. 2009, 5, 206-215
[e] Vossmeyer et al., Adv. Funct. Mater. 2008, 18, 1611-1616
[f] Herrmann et al., Appl. Phys. Lett. 2007, 91, 183105

Demonstrated herein is the use of the sensors and matrix of the present invention as highly sensitive strain gauges. Commercial strain gauges have typical gauge factor of 2. MCNP Strain gauges have adjustable gauge factor that is affected and can be controlled by the substrate thickness.

Example 6

Fatigue Properties of Flexible MCNP Sensors

Figure 14A:
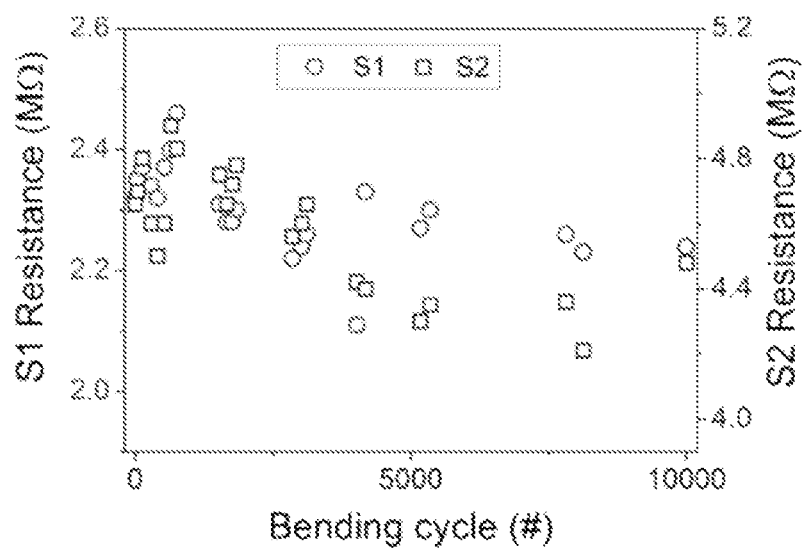
FIGS. 14A-14B.
Figure 14B:
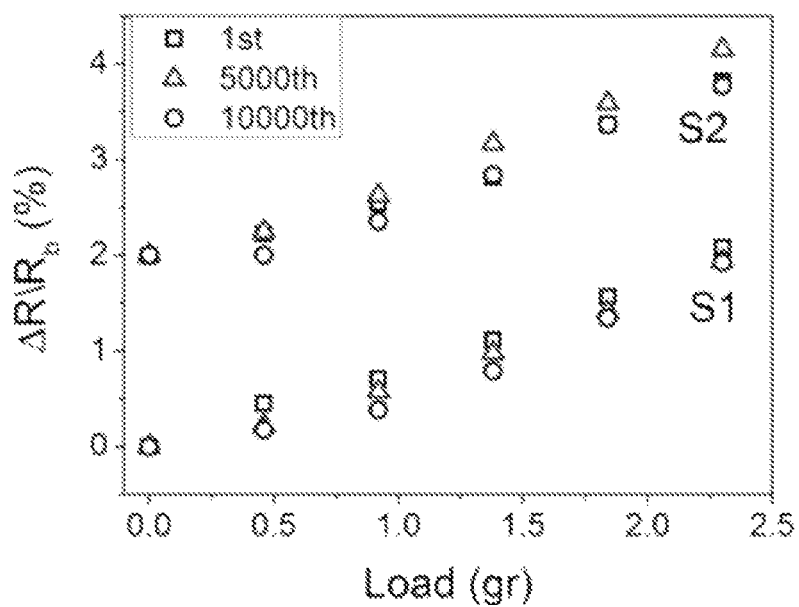

The fatigue properties over a large number of bending cycles were tested using three sensors on flexible Kapton® 127 substrate and ETP-MCNP as the sensing layer. The sensors were subjected to strains of 0.3% for 10,000 cycles. In one of the sensors, the baseline resistances changed dramatically and, therefore, the sensor was excluded. The other two sensors (S1 and S2) showed a drift in baseline resistance upon increasing the number of bending cycles (FIGS. 14A-14B). The maximum drift in the baseline resistance was ~9%. Without being bound by any theory or mechanism of action, while part of the drift could be attributed to the sensor per se, at least some of the drift could be attributed to changes in the temperature and relative humidity during the measurement. In contrast to the baseline resistance, the $\Delta R/R_b$ changed only slightly (2%) after 10,000 bending cycles. Thus, it is shown that the ETP-MCNP sensors exhibit excellent fatigue properties.

Example 7

Temperature and Humidity Sensing with Flexible MCNP Sensors

Figure 15A:
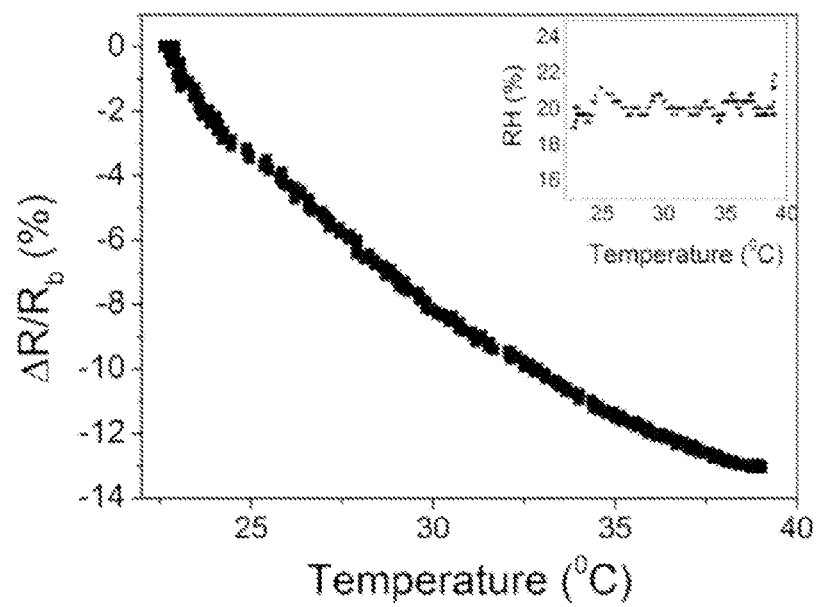
FIGS. 15A-15B.
Figure 15B:
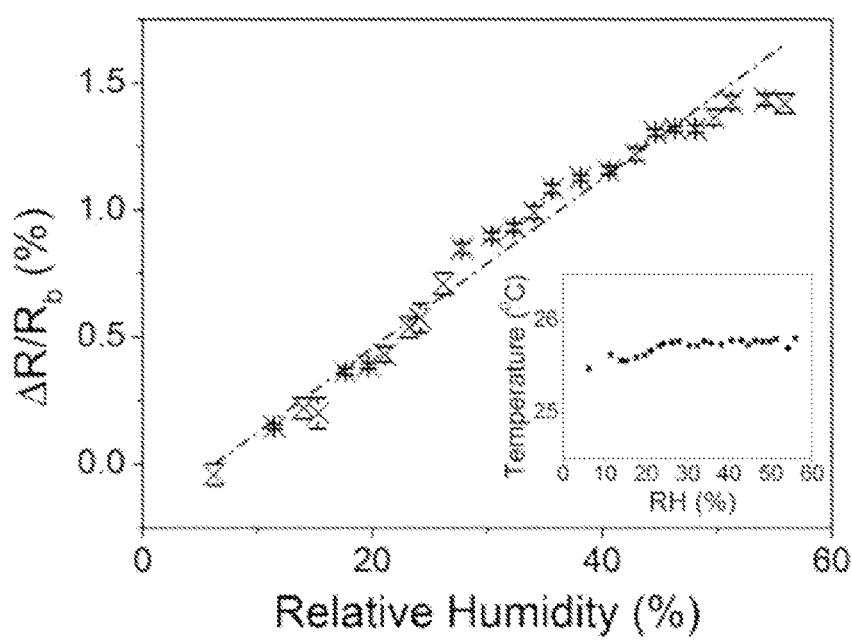

The possibility to integrate temperature and relative humidity (RH) sensing capabilities using the MCNP-based touch platforms was examined on an ETP-MCNP sensor mounted on a PET substrate. In order to test the sensor's responses to temperature and RH, the sensor was placed in a vacuum chamber having a controllable environment. The temperature and RH were altered separately, and the corresponding $\Delta R/R_b$ was monitored. FIG. 15A presents the $\Delta R/R_b$ of the sensor upon elevation of the temperature at a constant RH level of 20% (FIG. 15A, inset). The $\Delta R/R_b$ decreased exponentially with temperature (Wuelfing et al., J. Phys. Chem. B 2002, 106, 3139-3145). For practical purposes, the normalized resistance decreased by ~1% with each 1.66° C. increase in the temperature within a temperature range of 23-39° C. FIG. 15B shows $\Delta R/R_b$ of an ETP-MCNP-based sensor in a humidity region that exists in most environmental applications (5-60% RH). The sensor was tested at a constant temperature of 25.5° C. (FIG. 15B, inset). There exists an approximate linear increase in the sensing signal as a function of RH levels, with sensitivity that is down to a single percent RH.

Hence, it is contemplated that the sensitivity of the ETP-MCNP-based sensor is high enough to detect temperature fluctuations with a resolution less than 1° C. and humidity fluctuations with resolution of ~1% RH using a linear approximation of the sensor relative response. The sensors and platform of the present invention could therefore be used e.g. as a human body thermometer or sense a heat source in the vicinity of an artificial or electronic skin, without the need for touching the object.

Example 8

Touch Sensing Application

Figure 16A:
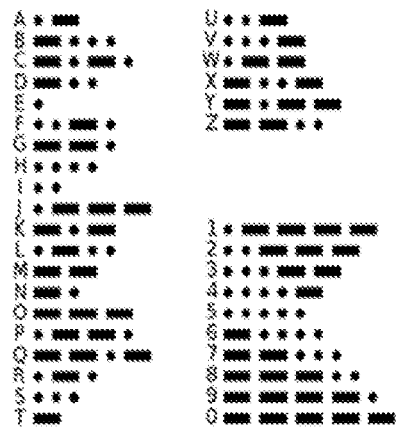
FIGS. 16A-16C.
Figure 16B:
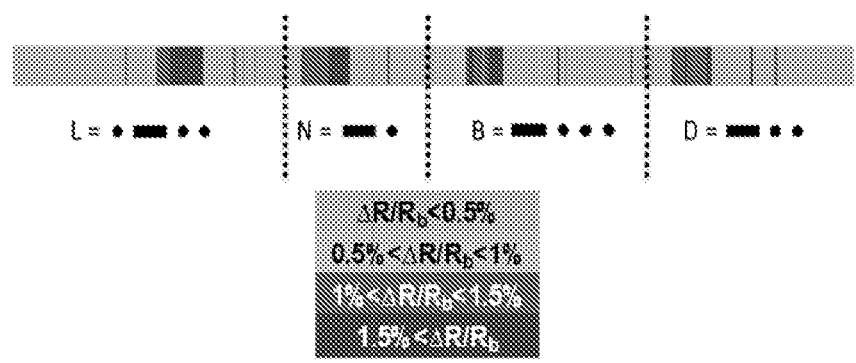
Figure 16C:
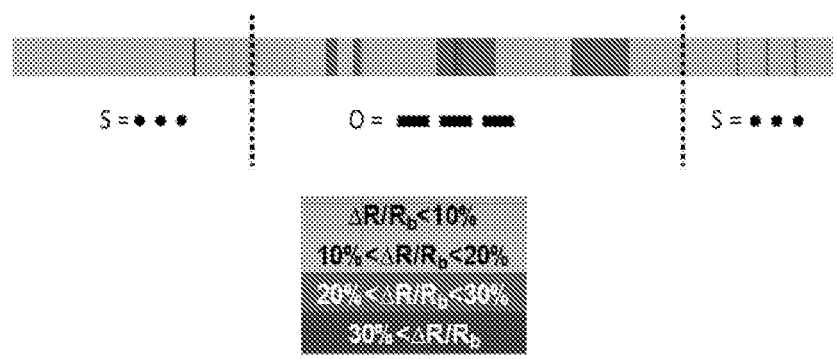

A demonstration of the ability of the MCNP sensors as touch sensors was performed by encoding letters using Morse code. Morse code is a combination of long and short pulses (lines and dots) that encode the entire alphabet and 10 digits (FIG. 16A). By pressing a finger on top of the sensor for short and long periods, a detection of these signals on each of the sensors was obtained. The electrical signal is translated to information on the pressure magnitude and duration of the pressure. Based on this mode of operation, two different signals (a short response in resistance which is defined as a dot, and a long response in resistance which is defined as a line) were obtained (the pressure was roughly estimated as a single KPa). A sensor of ETP-MCNP deposited on 125 μm thick PET substrate was used. The sensing layer of ETP-MCNP was facing down during the pressing so that no direct contact between the finger and the ETP-MCNP layer was formed. In this manner, the effect of the skin humidity and temperature on the sensing is minimized. Pressing on ETP-MCNP film that is deposited on 125 μm thick PET substrate produced robust, precise and repeatable signals (FIG. 16B). Similar results were obtained using DT-MCNP-based pressure sensors. Pressing on similar ERP-MCNP film that is deposited on a different substrate, namely a 36 μm thick Mylar®, produced x20-30 times higher responses (FIG. 16C). It is thus contemplated that the substrate's thickness largely affects sensor's responses.

It is therefore contemplated that load sensitivity can be adjusted by using different substrates. Accordingly, it is possible to design sensor matrices that are sensitive to different load ranges (e.g. suitable for small children as well as adults). Additional applications include intravascular neurosurgery where the sensing of load lower than 200 mg are required, a seat-belt sensor having small load sensitivity to transduce at loads larger than 1,000 Kg, or scoliosis surgery where high-load stress sensors are required.

Most touch panels today are based on an on/off sensing mechanisms were the devices are able to sense applied load but with no ability to determine the load (Walker, J. Soc. Info. Disp. 2012, 20, 413-440). The platform unit of the present invention has the capability of not merely to sense touch but also to sense the load magnitude. Using a variety of substrates allows tuning the sensing properties to specific load ranges that are required for a specific application.

Example 9

MCNP-based Sensing Platforms for Integrated Measurement of Pressure, Temperature and Humidity Sensing various parameters (e.g., pressure, temperature, humidity) from a complex sample using a single flexible sensing platform is demonstrated herein. A prototype based on MCNP technology was prepared and its abilities to measure the surrounding temperature, relative humidity and applied load were estimated. Different substrates were used in order to eliminate the load sensing from part of the sensors, and different capping ligands were chosen to isolate the sensing of relative humidity or temperature. Two sensors were fabricated by casting ETP-MCNP and NTMBT-MCNP on silicon dioxide with evaporated interdigitated gold electrode. A third sensor was fabricated by casting ETP-MCNPs on a PET substrate with 1 mm electrodes spacing as illustrated in FIG. 17.

Figure 18A:
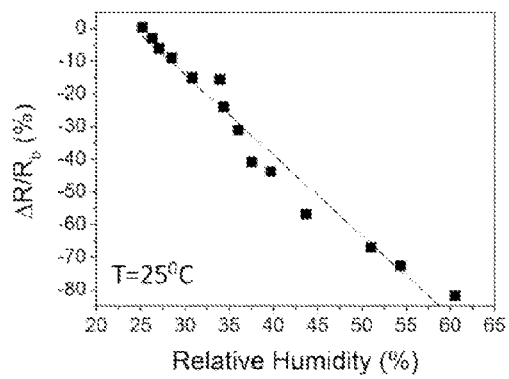
FIGS. 18A-18D: $\Delta R/R_b$ of a perforated NTMBT-MCNP sensor on a silicon dioxide substrate vs.
Figure 18B:
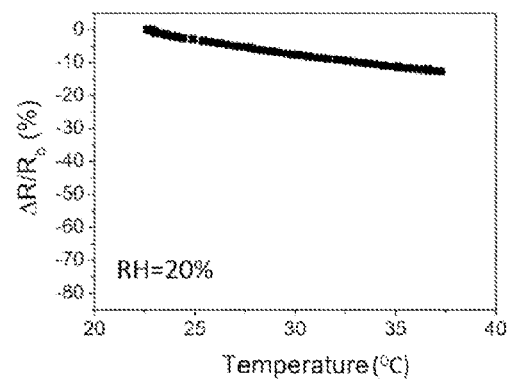
Figure 18C:
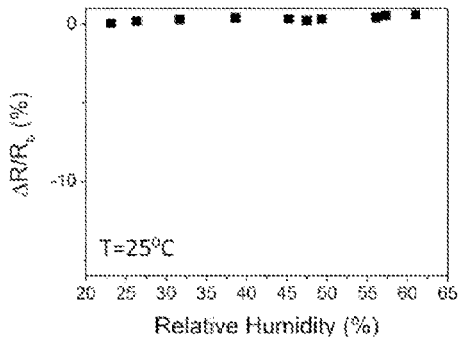
Figure 18D:
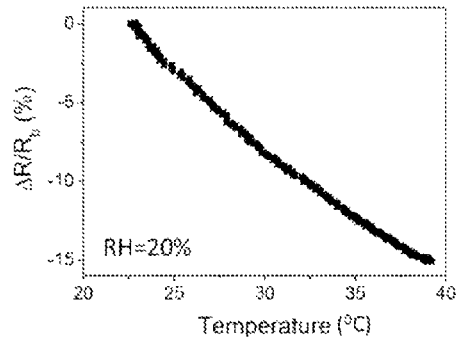

Temperature and humidity were calculated using the inflexible sensors. For sensing relative humidity, a perforated NTMBT-MCNP film was used as described in Segev-Bar et al., J. Phys. Chem. C. 2012, 116, 15361-15368; the content of which is hereby incorporated in its entirety. This sensor has a large negative response (up to 80%) to increasing levels of RH due to ionization mechanism. As can be seen in FIGS. 18A-18B, the relative response of NTMBT-MCNP to 55% RH is about −70% while the maximum relative response to temperature in the tested range (23-38° C.) was 15%. In order to sense mainly temperature changes, a high concentrated ETP-MCNP solution (50 mg/ml) was casted on silicon dioxide substrate, resulting in a film of 500 nm thickness (estimated by AFM). The film's thickness was higher than the thickness of the evaporated gold electrodes (350 nm) which may result in possible swelling (Steinecker et al., Anal. Chem. 2007, 79, 4977-4986). As seen in FIGS. 18C-18D, the response of the ETP-MCNP layer on the silicon dioxide substrate to relative humidity was within the noise range (±1%) for the entire relative humidity range (22-63% RH), while the relative response decreased when increasing the temperature ($\Delta R/R_b$~1.35% for each 1° C. change).

The prototype platform was exposed to different temperature and relative humidity cycles controlled by air conditioning in a room. The relative humidity range was 33-60% and the temperature range was 15-22° C. The relative humidity was modeled by a linear fit in FIG. 18A and the temperature was modeled by an Arrhenius fit in FIG. 18D. The average errors from the values measured by external sensors of 6 different cycles are summarized in Table 3. When averaging all cycles, the temperature average error was 4.8%±1.4% and the RH average error was 9.3%±7%.

TABLE 3

Summary of the accuracy for measuring temperature and RH using S1 and S2

| Cycle | Temperature average error (%) | RH average error (%) |
|---|---|---|
| 1 | 17.7 ± 2.6 | 5.8 ± 6.9 |
| 2 | 2.3 ± 1.2 | 20 ± 5.7 |
| 3 | 0.7 ± 0.6 | 10.7 ± 9.8 |
| 4 | 8 ± 1.4 | 5.8 ± 6 |
| 5 | 9.4 ± 1.5 | 6.6 ± 7.3 |
| 6 | 10.2 ± 1.3 | 7.8 ± 6.2 |

Figure 19A:
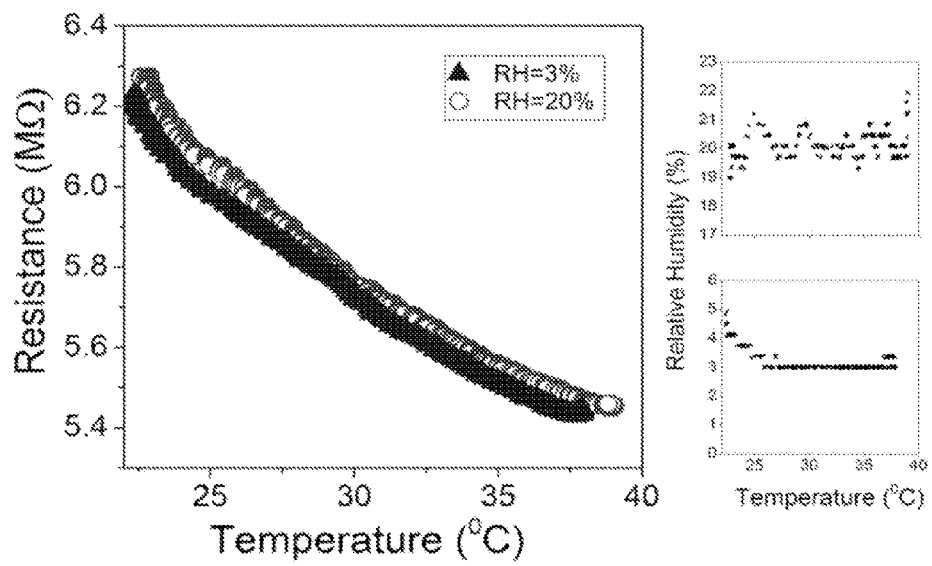
FIGS. 19A-19B.
Figure 19B:
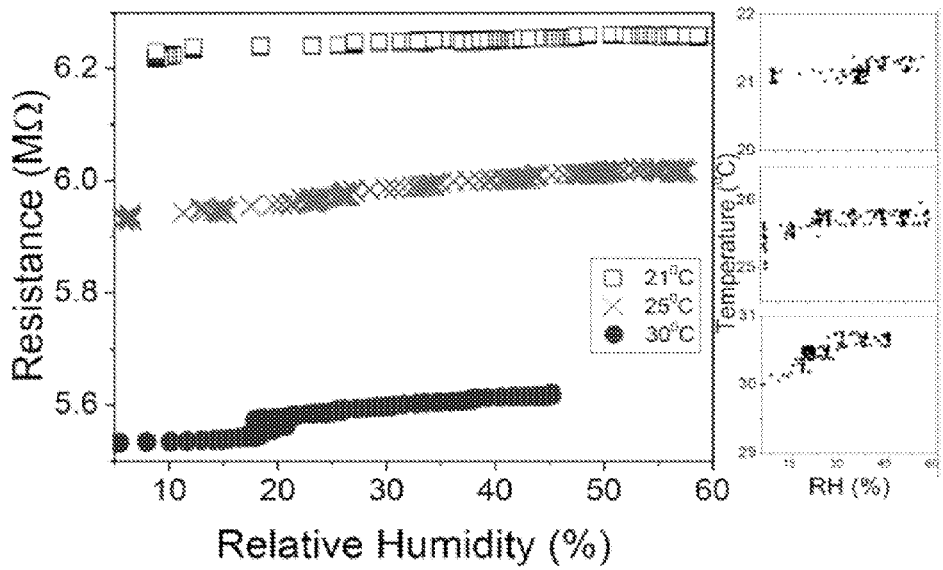

For assessing the performance of the prototype platform in sensing load, an unknown load was applied on the flexible ETP-MCNP sensor. For this purpose an algorithm that accounts for the temperature, RH and load is required. In general, the change in resistance of a given sensor is a factor of three parameters: temperature, RH and load. The effect of each parameter may be linear or non-linear. However, as disclosed herein, it is possible to model and measure a sensor's resistance due to changes in RH and temperature under a given load. To demonstrate the ability to easily model the effect of RH and temperature, several experiments were performed. The correlation between temperature and RH on the sensor's resistance was established by exposing the sensor to a range of temperatures (23-38° C.) at 2 different constant RH conditions (FIG. 19A) and exposing the sensor to a range of RHs (22-63%) at 3 constant temperatures (FIG. 19B). FIG. 19A shows the Arrhenius dependence of the sensor's response to various temperatures. The lines of the 2 different RH conditions are parallel. For small temperature ranges (~5° C.), the sensor's temperature dependence can be approximated as linear. FIG. 19B also exhibits mostly linear and parallel responses upon increasing RH levels (excluding the step in 20% RH at 30° C.). Since it was not possible to maintain constant conditions for RH >25% when changing the temperature, it is contemplated that this behavior represents the entire tested range (Konvalina et al., ACS Appl. Mater. Interf. 2012, 4, 317-325). The dependence of the ETP-MCNP sensor's response on temperature (T) and relative humidity (RH) can be approximately described in the following equation:

$$R = R_{baseline} + \Delta R_{RH} \cdot RH + \Delta R_T \cdot T$$

where R is the measured resistance of the sensor; $\Delta R_{RH}$ is the change in resistance per unity change in the relative humidity; $\Delta R_T$ is the change in resistance per unity change in the temperature; and $R_{baseline}$ is the extrapolated resistance under zero temperature and RH. A linear model was used for simplicity. Based on this equation, the response of the flexible ETP-MCNP sensor can be described as a plane in the resistance-temperature-RH space.

The three-sensor-based prototype was measured under changing environmental conditions as mentioned above. The flexible ETP-MCNP sensor was examined under different loads. The response of the flexible ETP-MCNP sensor to temperature ($\Delta R_T$) and relative humidity ($\Delta R_{RH}$) was different for different loads, and calculated using a solver script in Microsoft. The input parameters that were used are: the different environmental conditions (temperature and relative humidity) and the corresponding resistance of the flexible ETP-MCNP sensor.

Figure 20:
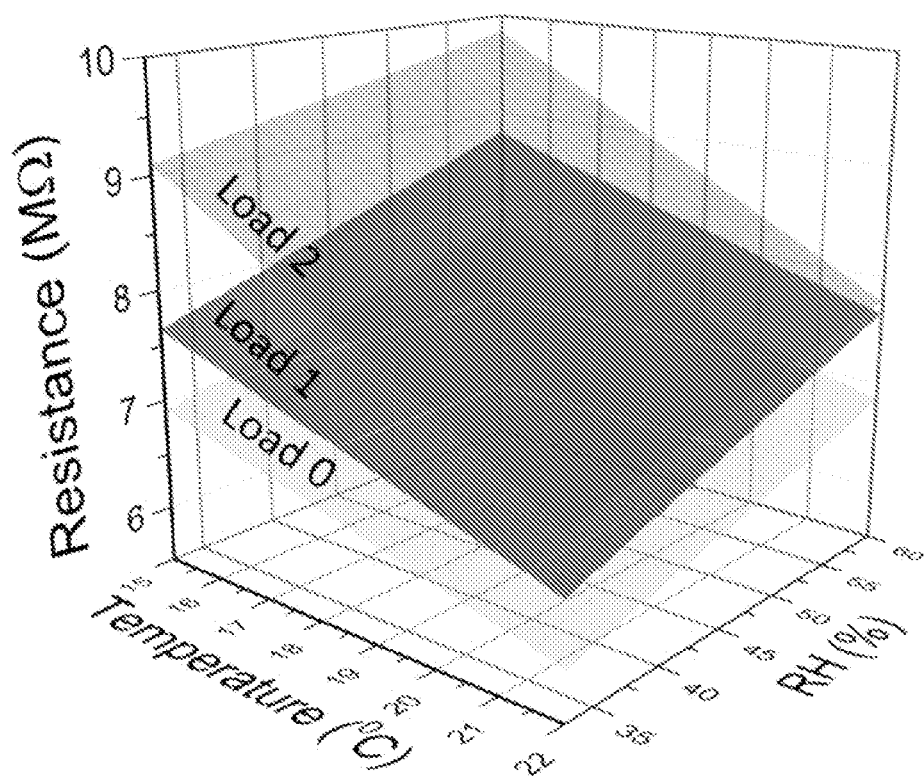
FIG. 20: Calculated planes for an ETP-MCNP sensor on a PET substrate for 3 different loads. Load 0: unloaded; Load 1: 3 gr load; and Load 2: 6 gr load. The temperature and RH were measured by the inflexible ETP-MCNP and NTMBT-MCNP sensors. The parameters were calculated using solver script in excel.

FIG. 20 describes the different dependencies of the flexible ETP-MCNP sensor at the temperature and relative humidity under zero load (Load 0), load of 3 gr (Load 1) and a load of 6 gr (Load 2). The temperature and relative humidity were calculated by the inflexible ETP-MCNP and NTMBT-MCNP sensors (FIGS. 18A-18D and 19A-19B). As can be seen in FIG. 20, the relative response to temperature and relative humidity changed when different loads were applied (e.g. $\Delta R_{RH}$ and $\Delta R_T$ were dependent on the load).

TABLE 4

Calculated and applied loads on an ETP-MCNP sensor deposited on a PET substrate.

| Applied Load | Calculated load | | |
|---|---|---|---|
| | 18.7° C., 47% RH | 19.7° C., 45% RH | 21.4° C., 43.5% RH |
| 3 gr | 2.42 gr | 2.8 gr | 3.07 gr |
| 6 gr | 6.7 gr | 6.68 gr | 6.08 gr |

The accuracy of the model was estimated by measuring the load sensitivity of the ETP-MCNP sensor on PET substrate at specific temperatures and RHs, calculating the relative response of the sensor at these environmental conditions based on the plans that are presented in FIG. 20, and calculating the applied force based on the data. The results are summarized in Table 4. The results clearly demonstrate the ability of the model to estimate the load with less than 20% variance.

The matrix prototype presented herein uses different MCNP on inflexible substrate in order to sense temperature and humidity in an un-conjugated manner (were a single sensor senses only either temperature or relative humidity). A post measurement algorithm was used for the flexible ETP-MCNP sensor in order to isolate load sensing from other parameters (temperature and humidity). When load was applied, the enlarging distance between the nanoparticles changed the surface coverage which resulted in a change in morphology. These changes affect the MCNP sensor response. In instances where the effect of temperature and RH on resistance is not linear, it is possible to model the correlation, and draw representative non-linear planes that would enable the measurements of the desired parameter.

Example 10

Figure 21A:
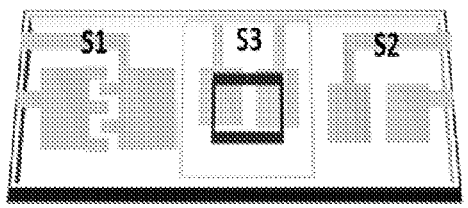
FIGS. 21A-21C.
Figure 21B:
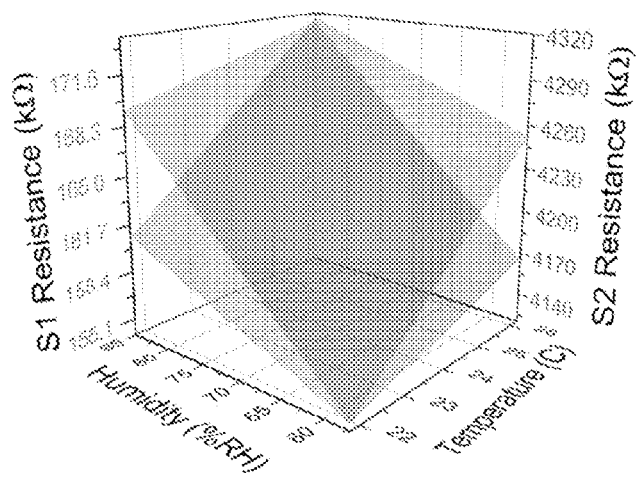

Integration of Load, Temperature and RH Sensors (3 in 1) Via Layer-by-Layer Deposition Gold nanoparticles coated with dodecylamine (DA-GNPs) were deposited via the layer-by-layer (LBL) technique (Joseph et al., J. Phys. Chem. C. 2007, 111, 12855-12859; and Vossmeyer et al., Adv. Funct. Mater. 2008, 18, 1611-1616) on a Kapton® substrate having two electrode pairs with different shapes and spaces (S1 and S2). S1 had an interdigitated structure of 10 pairs of Au electrodes (100 µm width and 100 µm spacing between adjacent electrodes). S2 and S3 had 2 electrodes with 100 µm spacing between them. The use of different pairs of electrodes resulted in different baseline resistances for S1 and S2 (~150 KΩ for S1 and ~4100 KΩ for S2). Hence, by fabricating the environmental sensors using different electrode structures, different responses to temperature and humidity are obtained. S3 was placed facing down towards the table assuring partial shielding from the environment. A small window engraved into the substrate allowed physical sinking when the sensor was pressed towards the table (FIG. 21A). The sensors' resistance was measured at room environmental conditions. The temperature and relative humidity of the room were recorded by separate (external) sensors. Separating the three features (pressure, relative humidity and temperature) was performed as follows: Both S1 and S2 were measured under varying conditions. The experimental temperature range was 21.5° C.-26° C. and the relative humidity range was 55-85%. Post-measurement algorithmic calculations were used to calculate the RH and T parameters while the third environmental protected sensor was set to simultaneously sense touch. The dependency of each sensor i on the temperature ($\Delta R_{iT}$) and relative humidity ($\Delta R_{iRH}$) was different due to the different electrodes' structure, and calculated using a solver script in Microsoft Excel based on 13 measurement sets. As an input, the different environmental conditions (temperature and relative humidity) and the corresponding resistance of each of the two sensors were used in the following equation:

$$R_i = R_{ibaseline} + \Delta R_{iRH} \cdot RH + \Delta R_{iT} \cdot T$$

where $R_i$ is the measured resistance of sensor i under certain RH and temperature (T) conditions, and $R_{ibaseline}$ is the extrapolated resistance under zero temperature and RH. Based on the two sensors that create different planes in the resistance-temperature-RH space, the temperature and the relative humidity was calculated in an injective manner (FIG. 21B).

TABLE 5

Summary of the model's accuracy for temperature and RH sensing with S1 and S2

| Measured temperature (° C.) | Calculated temperature (° C.) | % deviation | Measured RH (%) | Calculated RH (%) | Deviation (%) |
|---|---|---|---|---|---|
| 22.1 | 22 | 0.5 | 59.2 | 58.6 | 1 |
| 23.7 | 23.3 | 1.7 | 82 | 84.7 | 3.3 |
| 25.3 | 25.4 | 0.4 | 83 | 83.1 | 0.1 |

Figure 21C:
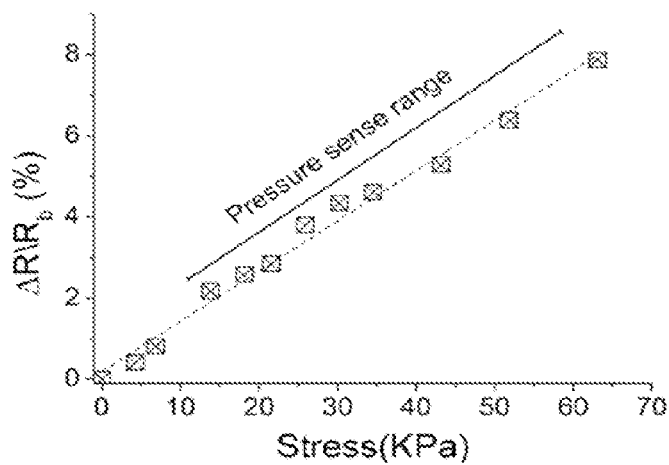

In order to test the accuracy of the received model, three additional points of resistance under different environmental conditions were measured by an external sensor and calculated through the fitted equations. The results are presented in Table 5. The middle sensor facing down (S3) was less sensitive to the variations in humidity and temperature, where the effect on the resistance was less than 1% throughout the entire experiment. In comparison, when applying pressures of about 15 KPa, the response due to bending of the substrate was about 2% (FIG. 21C). Thus, it is possible to sense pressure using S3 with detection limit of 15 KPa, since the effects of temperature and relative humidity on the sensor are insignificant when comparing the magnitude of the signal that was obtained by the applied pressure. Thus, for pressures higher than 15 KPa, the noise as a result of changing the environmental conditions is negligible and the pressure can be easily measured. The model can estimate the surrounding temperature and relative humidity (Table 5). Therefore, by combining three sensors with similar nanoparticle coating and controlling the electrodes shape and direction it is possible to measure all three parameters.

Hence, by using an array of 3 sensors in which the load sensor is protected from environmental effects and the other two sensors are protected from mechanical deflection, multi-parametric sensing can be obtained. These results demonstrate the possibility of producing and integrating temperature and humidity sensors as part of an artificial or electronic skin application based on MCNPs. Thus, it is possible to use a single (or similar) MCNP chemistry with various substrate structures/designs to achieve multi-parametric sensing such as temperature, relative humidity and load, on the same platform.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A platform unit for detecting a parameter selected from the group consisting of pressure, temperature, humidity and a combination thereof, the platform unit comprising at least three sensors comprising metallic nanoparticles capped with an organic coating, wherein the three sensors comprise:
    a pressure sensor being deposited on a substantially flexible substrate, wherein the pressure sensor is configured to sense pressure applied thereon and to generate an electrical signal in response thereto,
    a temperature sensor configured to exhibit a change in conformation of the metallic nanoparticles capped with an organic coating in response to a change in temperature and generate an electrical signal in response thereto, and
    a humidity sensor configured to exhibit a change in conformation of the metallic nanoparticles capped with an organic coating in response to a change in humidity and generate an electrical signal in response thereto,
    thereby providing the detection of pressure, temperature, humidity or their combination.

2. The platform unit according to claim 1 further comprising a plurality of electrodes comprising an electrically conductive material, wherein the plurality of electrodes are coupled to each sensor and are used for measuring the signals generated by the sensors.

3. The platform unit according to claim 1 further comprising a detection means comprising a device for measuring changes in at least one of resistance, conductance, alternating current (AC), frequency, capacitance, impedance, inductance, mobility, electrical potential, optical property or voltage threshold.

4. The platform unit according to claim 1, wherein each sensor is configured in a form selected from the group consisting of a capacitive sensor, a resistive sensor, a chemiresistive sensor, an impedance sensor, and a field effect transistor sensor.

5. The platform unit according to claim 1 further comprising a film, wherein the film is configured to block at least one sensor from generating a signal in response to a change in humidity.

6. The platform unit according to claim 5, wherein the film is characterized by a thickness ranging from about 1 μm to about 1000 μm.

7. The platform unit according to claim 5, wherein the film is selected from the group consisting of an epoxy resin, a silicon resin, a polyamide resin, a polyimide resin, a poly(p-xylylene) resin and a combination thereof.

8. The platform unit according to claim 1, wherein the substantially flexible substrate is characterized by widths in the range of about 0.01-10 cm and thicknesses in the range of about 20-500 μm.

9. The platform unit according to claim 1, wherein the substantially flexible substrate comprises a polymer.

10. The platform unit according to claim 9, wherein the polymer is selected from the group consisting of polyimide, polyamide, polyimine, polyethylene, polyester, polydimethylsiloxane, polyvinyl chloride, and polystyrene.

11. The platform unit according to claim 1, wherein the temperature or humidity sensor is deposited on a substantially flexible or substantially rigid substrate.

12. The platform unit according to claim 1, wherein i) the temperature sensor is deposited on a substantially rigid substrate, or ii) wherein the humidity sensor is deposited on a substantially rigid substrate.

13. The platform unit according to claim 12, wherein the substantially rigid substrate is selected from the group consisting of metals, insulators, semiconductors, semimetals, and combinations thereof.

14. The platform unit according to claim 1, wherein the metallic nanoparticles are selected from the group consisting of Au, Ag, Ni, Co, Pt, Pd, Cu, Al, and combinations thereof or wherein the metallic nanoparticles are metallic alloys selected from the group consisting of Au/Ag, Au/Cu, Au/Ag/Cu, Au/Pt, Au/Pd, Au/Ag/Cu/Pd, Pt/Rh, Ni/Co, and Pt/Ni/Fe.

15. The platform unit according to claim 1, wherein the organic coating comprises compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof.

16. The platform unit according to claim 1, wherein the humidity sensor comprises continuous and discontinuous regions of metallic nanoparticles capped with an organic coating.

17. The platform unit according to claim 16, wherein the discontinuous regions comprise voids ranging in size from about 10 nm to about 500 nm.

18. The platform unit according to claim 17, wherein the discontinuous regions comprise between about 3% and about 90% voids.

19. The platform unit according to claim 1, integrated on electronic or artificial skin surface.

* * * * *